United States Patent
Aceti et al.

(10) Patent No.: US 6,923,764 B2
(45) Date of Patent: Aug. 2, 2005

(54) ANALYTE MONITOR

(75) Inventors: John Gregory Aceti, Cranbury, NJ (US); Zvi Gerald Loewy, Fair Lawn, NJ (US); Richard Morgan Moroney, III, Princeton, NJ (US); Christopher Carter Gregory, Newtown, PA (US); Peter John Zanzucchi, West Windsor, NJ (US)

(73) Assignee: Rosedale Medical, Inc., Cupertino, CA (US)

( * ) Notice: Subject to any disclaimer, the term of this patent is extended or adjusted under 35 U.S.C. 154(b) by 255 days.

(21) Appl. No.: 10/347,620

(22) Filed: Jan. 22, 2003

(65) Prior Publication Data

US 2003/0135333 A1 Jul. 17, 2003

Related U.S. Application Data

(63) Continuation of application No. 09/741,755, filed on Dec. 20, 2000, now Pat. No. 6,540,675.
(60) Provisional application No. 60/214,334, filed on Jun. 27, 2000.

(51) Int. Cl.[7] ................................................. A61B 5/00
(52) U.S. Cl. ....................................... 600/309; 600/310
(58) Field of Search ................................ 600/309, 310, 600/316, 322, 347, 573, 575, 583, 577, 556, 578, 584; 436/95; 422/68.1, 82.05, 82.06, 82.07, 82.08

(56) References Cited

U.S. PATENT DOCUMENTS

| | | |
|---|---|---|
| 4,057,394 A | 11/1977 | Genshaw |
| 4,254,083 A | 3/1981 | Columbus |
| 4,258,001 A | 3/1981 | Pierce et al. |
| 4,321,397 A | 3/1982 | Nix et al. |
| 4,350,762 A | 9/1982 | De Luca et al. |
| 4,394,512 A | 7/1983 | Batz |
| 4,418,037 A | 11/1983 | Katsuyama et al. |
| 4,737,458 A | 4/1988 | Batz et al. |
| 4,774,192 A | 9/1988 | Terminiello et al. |
| 4,790,979 A | 12/1988 | Terminiello et al. |

(Continued)

FOREIGN PATENT DOCUMENTS

| | | |
|---|---|---|
| WO | WO 97/15227 | 5/1997 |
| WO | WO 97/29847 | 8/1997 |
| WO | WO 98/31275 | 7/1998 |
| WO | WO 00/14269 | 3/2000 |
| WO | WO 00/14535 | 3/2000 |

(Continued)

OTHER PUBLICATIONS

The Diabetes Control and Complications Trial Research Group, "The effect of intensive treatment of diabetes on the development and progression of long-term complications in insulin-dependent diabetes mellitus." New Engl. J. Med. 1993; 329:977–986.

(Continued)

Primary Examiner—Eric F. Winakur
(74) Attorney, Agent, or Firm—Patton Boggs LLP

(57) ABSTRACT

Provided is an analyte monitoring device having a housing, the device comprising: a plurality of needles, each having a tip, a retracted position, a position wherein the tip is extended from the housing a distance adapted to pierce skin; an electrically or spring powered needle pushing apparatus movable to separately engage each of the needles to move each from the retracted position to the extended position; an energy source located within the housing; a plurality of analysis sites comprising an analysis preparation, each adapted to receive liquid from the needles to wet the analysis preparation; one or more light sources adapted to direct light at the analysis sites; one or more light detectors adapted to receive light from the analysis sites; and a processor.

97 Claims, 11 Drawing Sheets

U.S. PATENT DOCUMENTS

| | | | |
|---|---|---|---|
| 4,794,926 A * | 1/1989 | Munsch et al. ............ 606/183 |
| 4,953,552 A | 9/1990 | De Marzo |
| 4,966,646 A | 10/1990 | Zdeblick |
| 5,059,394 A | 10/1991 | Phillips et al. |
| 5,077,199 A | 12/1991 | Basagni et al. |
| 5,094,943 A | 3/1992 | Siedel et al. |
| 5,116,759 A | 5/1992 | Klainer et al. |
| 5,141,868 A | 8/1992 | Shanks et al. |
| 5,174,291 A | 12/1992 | Schoonen et al. |
| 5,176,632 A * | 1/1993 | Bernardi .................... 600/347 |
| 5,179,005 A | 1/1993 | Phillips et al. |
| 5,183,741 A | 2/1993 | Arai et al. |
| 5,196,302 A | 3/1993 | Kidwell |
| 5,208,163 A | 5/1993 | Charlton et al. |
| 5,213,966 A | 5/1993 | Vuorinen et al. |
| 5,234,818 A | 8/1993 | Zimmermann et al. |
| 5,251,126 A | 10/1993 | Kahn et al. |
| 5,278,079 A | 1/1994 | Gubinski et al. |
| 5,288,646 A | 2/1994 | Lundsgaard et al. |
| 5,302,513 A | 4/1994 | Mike et al. |
| 5,304,468 A | 4/1994 | Phillips et al. |
| 5,306,623 A | 4/1994 | Kiser et al. |
| 5,308,767 A | 5/1994 | Terashima |
| 5,360,595 A | 11/1994 | Bell et al. |
| 5,383,512 A | 1/1995 | Jarvis |
| 5,451,350 A | 9/1995 | Macho et al. |
| 5,458,140 A | 10/1995 | Eppstein et al. |
| 5,460,777 A | 10/1995 | Kitajima et al. |
| 5,507,288 A | 4/1996 | Böcker et al. |
| 5,568,806 A | 10/1996 | Cheney, II et al. |
| 5,577,499 A | 11/1996 | Teves |
| 5,582,184 A | 12/1996 | Erickson et al. |
| 5,591,139 A | 1/1997 | Lin et al. |
| 5,632,410 A * | 5/1997 | Moulton et al. ............ 221/79 |
| 5,636,632 A | 6/1997 | Bommannan et al. |
| 5,658,515 A | 8/1997 | Lee et al. |
| 5,676,850 A | 10/1997 | Reed et al. |
| 5,680,858 A | 10/1997 | Hansen et al. |
| 5,681,484 A | 10/1997 | Zanzucchi et al. |
| 5,682,233 A | 10/1997 | Brinda |
| 5,697,901 A | 12/1997 | Eriksson |
| 5,705,018 A | 1/1998 | Hartley |
| 5,735,273 A | 4/1998 | Kurnik et al. |
| 5,741,211 A | 4/1998 | Renirie et al. |
| 5,746,217 A | 5/1998 | Erickson et al. |
| 5,771,890 A | 6/1998 | Tamada |
| 5,801,057 A | 9/1998 | Smart et al. |
| 5,820,570 A | 10/1998 | Erickson et al. |
| 5,827,183 A | 10/1998 | Kurnik et al. |
| 5,840,020 A | 11/1998 | Heinonen et al. |
| 5,855,801 A | 1/1999 | Lin et al. |
| 5,858,194 A | 1/1999 | Bell |
| 5,866,281 A | 2/1999 | Guckel et al. |
| 5,879,310 A | 3/1999 | Sopp et al. |
| 5,879,326 A | 3/1999 | Godshall et al. |
| 5,879,367 A | 3/1999 | Latterell et al. |
| 5,893,870 A | 4/1999 | Talen et al. |
| 5,911,737 A | 6/1999 | Lee et al. |
| 5,912,139 A | 6/1999 | Iwata et al. |
| 5,925,021 A | 7/1999 | Castellano et al. |
| 5,928,207 A | 7/1999 | Pisano et al. |
| 5,954,685 A | 9/1999 | Tierney |
| 5,971,941 A | 10/1999 | Simons et al. |
| 5,972,294 A | 10/1999 | Smith et al. |
| 5,989,409 A | 11/1999 | Kurnik et al. |
| 5,993,189 A | 11/1999 | Mueller et al. |
| 6,001,067 A | 12/1999 | Shults et al. |
| 6,010,463 A | 1/2000 | Lauks et al. |
| 6,014,577 A | 1/2000 | Henning et al. |
| 6,023,629 A | 2/2000 | Tamada |
| 6,030,827 A | 2/2000 | Davis et al. |
| 6,032,059 A | 2/2000 | Henning et al. |
| 6,041,253 A | 3/2000 | Kost et al. |
| 6,050,988 A | 4/2000 | Zuck |
| 6,056,734 A | 5/2000 | Jacobsen et al. |
| 6,059,815 A | 5/2000 | Lee et al. |
| 6,077,660 A | 6/2000 | Wong et al. |
| 6,080,116 A | 6/2000 | Erickson et al. |
| 6,083,196 A | 7/2000 | Trautman et al. |
| 6,090,790 A | 7/2000 | Eriksson |
| 6,091,975 A | 7/2000 | Daddona et al. |
| 6,100,107 A | 8/2000 | Lei et al. |
| 6,102,933 A | 8/2000 | Lee et al. |
| 6,103,033 A | 8/2000 | Say et al. |
| 6,103,197 A | 8/2000 | Werner |
| 6,106,751 A | 8/2000 | Talbot et al. |
| 6,118,126 A | 9/2000 | Zanzucchi |
| 6,120,676 A | 9/2000 | Heller et al. |
| 6,123,861 A | 9/2000 | Santini, Jr. et al. |
| 6,126,899 A | 10/2000 | Woudenberg et al. |
| 6,132,449 A | 10/2000 | Lum et al. |
| 6,142,939 A | 11/2000 | Eppstein et al. |
| 6,175,752 B1 | 1/2001 | Say et al. |
| 6,183,434 B1 | 2/2001 | Eppstein et al. |
| 6,187,210 B1 | 2/2001 | Lebouiz et al. |
| 6,192,891 B1 | 2/2001 | Gravel et al. |
| 6,200,296 B1 | 3/2001 | Dibiasi et al. |
| 6,206,841 B1 | 3/2001 | Cunningham et al. |
| 6,214,626 B1 | 4/2001 | Meller et al. |
| 6,219,574 B1 | 4/2001 | Cormier et al. |
| 6,230,051 B1 | 5/2001 | Cormier et al. |
| 6,242,207 B1 | 6/2001 | Douglas et al. |
| 6,245,215 B1 | 6/2001 | Douglas et al. |
| 6,251,083 B1 | 6/2001 | Yum et al. |
| 6,251,260 B1 | 6/2001 | Heller et al. |
| 6,255,061 B1 | 7/2001 | Mori et al. |
| 6,256,533 B1 | 7/2001 | Yuzhakov et al. |
| 6,272,364 B1 | 8/2001 | Kurnik |
| 6,298,254 B2 | 10/2001 | Tamada |
| 6,299,578 B1 | 10/2001 | Kurnik et al. |
| 6,309,351 B1 | 10/2001 | Kurnik et al. |
| 6,312,612 B1 | 11/2001 | Sherman et al. |
| 6,322,808 B1 | 11/2001 | Trautman et al. |
| 6,329,161 B1 | 12/2001 | Heller et al. |
| 6,331,266 B1 | 12/2001 | Powell et al. |
| 6,332,871 B1 | 12/2001 | Douglas et al. |
| 6,334,856 B1 | 1/2002 | Allen et al. |
| 6,350,273 B1 | 2/2002 | Minagawa et al. |
| 6,356,776 B1 | 3/2002 | Berner et al. |
| 6,530,892 B1 | 3/2003 | Kelly |
| 6,540,675 B2 * | 4/2003 | Aceti et al. ................. 600/309 |
| 2001/0001034 A1 | 5/2001 | Douglas |
| 2001/0053891 A1 | 12/2001 | Ackley |
| 2002/0002326 A1 | 1/2002 | Causey, III et al. |
| 2002/0002344 A1 | 1/2002 | Douglas et al. |
| 2002/0004640 A1 | 1/2002 | Conn et al. |
| 2002/0006355 A1 | 1/2002 | Whitson |
| 2002/0016568 A1 | 2/2002 | Lebel et al |
| 2002/0020688 A1 | 2/2002 | Sherman et al. |
| 2002/0136667 A1 | 9/2002 | Subramanian et al. |
| 2002/0137998 A1 | 9/2002 | Smart et al. |
| 2002/0160520 A1 | 10/2002 | Orloff et al. |
| 2002/0177761 A1 | 11/2002 | Orloff et al. |

FOREIGN PATENT DOCUMENTS

| | | |
|---|---|---|
| WO | WO 00/18449 | 4/2000 |
| WO | WO 00/78208 | 12/2000 |
| WO | WO 01/16575 | 3/2001 |
| WO | WO 01/52727 | 7/2001 |
| WO | WO 01/64105 | 9/2001 |
| WO | WO 01/80728 | 11/2001 |

| | | |
|---|---|---|
| WO | WO 01/91634 | 12/2001 |
| WO | WO 02/49507 A1 | 6/2002 |
| WO | WO 02/49509 A2 | 6/2002 |

OTHER PUBLICATIONS

S. Coster et al., "Monitoring blood glucose control in diabetes mellitus: a systematic review." Health Technology Assessment 4(12) 2000.

W.H. Smart et al., "The use of silicon microfabrication technology in painless glucose monitoring." Diabetes Technology & Therapeutics 2:4, 549(2000).

M. Beregszaszi et al., "Nocturnal hypoglycemia in children and adolescents with insulin–dependent diabetes mellitus: prevalence and risk factors." J. Pediatr. Jul. 1997; 131 (1 Pt.1): 27–33.

H.P. Chase, "Continuous subcutaneous glucose monitoring in children with type 1 diabetes;." Pediatrics Feb. 2001; 107(2)222–6.

Andrew Spielman, "Mosquito—A natural history of our most persistent and deadly foe." Sc. D., Hyperion.

Su Yum, "Capillary blood sampling for self–monitoring of blood glucose." Diabetes Technology & Therapeutics vol. 1, Nov. 1, 1999.

P. Trinder, "Determination of glucose in blood using glucose oxidase with an alternate oxygen acceptor." Ann. Clin. Biochem. 6(1969) 24.

O. Sonntag, dry chemistry, Analysis with carrier –bound reagents, 1993 Elsevier Science Publishers, see p. 181.

ADA Self Monitoring of Blood Glucose, A Consensus Development Conference, Diabetes Care 1994::7:81:–6.

R.N. Johnson et al., "Accuracy of devices used for self–monitoring of blood glucose." Ann. Clin. Biochem. 1998:35:68–74.

R.N. Johnson et al., "Analytical error of home glucose monitors: a comparison of 18 systems." Ann. Clin. Biochem. 1999:36:72–9.

R.N. Johnson et al., "Error detection and measurement in glucose monitors." Clin. Chim. Acta. 2001:307(1–2):61–7.

W.L. Clarke et al., "Evaluating clinical accuracy of systems for self–monitoring of blood glucose." Diabetes Care 1987: 10: 622–8.

D.J. Cox et al., "Understanding error grid analysis." Diabetes Care 1997:20:911–12.

B. Feldman et al., "FreeStyle™: A Small–Volume Electrochemical Glucose Sensor for Home Blood Glucose Testing." Diabetes Technology and Therapeutics 2000:2(2):221–229.

E. Otto et al, "An intelligent diabetes software prototype: predicting blood glucose levels and recommending regimen changes." Diabetes Technology and Therapeutics 2000:2(4):569–576.

McGarraugh G. et al., "Physiological influences on off–finger glucose testing." Diabetes Technology and Therapeutics 2001 Fall; 3(3):367–76.

Rosen, "Road to New–Age Glucose Monitoring Still Rocky,." Diagnostic Insight, Summer 1999, pp. 4–5, 12–13, 16.

Mahler et al., "Clinical Review 102 Type 2 Diabetes Mellitus: Update on Diagnosis, Pathophysiology, and Treatment", The Journal of Clinical Endocrinology and Metabolism, 84: 1165–1170, 1999.

McNichols et al., "Optical glucose sensing in biological fluids: an overview." Journal of Biomedical Optics, 5(1), 5–16, Jan. 2000.

D'Arrigo, "GlucoWatch Monitor Poised for Approval." Diabetes Forecast, Mar. 2000, 43–44.

Svedman et al, "Skin mini–erosion technique for monitoring metabolites in interstitial fluid: its feasibility demonstrated by OGTT results in diabetic and non–diabetic subjects." Scand J Clin Lab Invest, 59(2):115–23, Apr. 1999.

Rebrin et al., "Subcutaneous glucose predicts plasma glucose independent of insulin: implications for continuous monitoring." Am J Physiol 277 (3 pt. 1): E561–71, Sep. 1999.

Collison et al. "Analytical characterization of electrochemical biosensor test strips for measurement of glucose in low–volume Interstitial fluid samples." Clin Chem. 45(9):1665–73, Sep. 1999.

Pfohl et al., "Spot glucose measurement in epidermal interstitial fluid—an alternative to capillary blood glucose estimation?" Exp Clin Endocrinal Diabetes, 108(1):1–4, 2000.

Kumetrix, Inc., "Painless blood glucose monitoring, courtesy of the mosquito." Start–Up, p. 27, Dec. 1999.

"Taking the 'ouch' out of needles: arrays of 'microneedles' offer new technique for drug delivery." Science Daily, 1999.

integonline.com; Integ website, LifeGuide Glucose Meter No lancets. No. Blood, 2000.

* cited by examiner

ANALYTE MONITOR

This application is a continuation of application Ser. No. 09/741,755, filed on Dec. 20, 2000, now U.S. Pat. No. 6,540,675, which claims benefit of 60/214,334, filed Jun. 27. 2000.

While efforts have been undertaken to increase the ease with which analytes from body fluids, such as glucose, can be periodically monitored. No proposed solution has proved entirely satisfactory. The present invention provides a new monitoring device which allows convenient such monitoring with reduced pain.

Diabetes mellitus, a disease in which the pancreas fails to produce insulin or cells fail to respond to insulin for cellular metabolism of glucose, is a world-wide public health problem in terms of loss of quality of life and corresponding cost of care.

The World Health Organization estimates, as of 1994, there are 110 million diabetics worldwide with 14–16 million in the USA. This number is increasing and expected to double by 2030. Approximately 12–14 million diabetics are classified as noninsulin dependent, or Type II, diabetics who can control their glucose levels by changes in life style, by the use of medication or by the infrequent use of insulin. For approximately 1–2 million diabetics, classified as Type I diabetics, injections of insulin are needed to maintain glucose levels. Data from the Diabetes Control and Complications Trial (DCCT), reported in 1993, show that the quality of life may significantly be improved for people with diabetes if good control of blood sugar (glucose) levels is maintained. Thus, there is a need for frequent and accurate self-testing of glucose.

To meet this need, the most widely used, reliable and accurate method is a direct assay for glucose in a small amount of, typically, venous blood. Hand-held instruments, which measure the amount of glucose based on the interaction of glucose with reagents predeposited on test strips, are now widely available. Typically these instruments detect the amount of glucose in blood to plus or minus 4%, based on specific enzymatic reactions using microliter samples of blood.

While the chemistry for these test are reliable, and the manufacturers of the test strips have demonstrated good quality control, current self-testing remains a conscious process in which the diabetic must elect to take a blood sample and do the assay protocol for the hand-held instrument of choice. The primary failure for diabetics to do frequent self-testing for blood glucose levels, as recommend by the conclusions of the DCCT, is the pain associated with obtaining blood samples on a frequent schedule as well as the inconvenience of this, particularly in public places.

To reduce pain and inconvenience, blood glucose assays based on interstitial fluid, on transport through the skin (iontophoresis) and by implanted glucose sensors are technologies currently proposed, in development, or FDA approved. Cygnus, Inc. (Redwood, Calif.) has received FDA approval for the "GlucoWatch" a noninvasive glucose testing device that is based on electrode-driven iontophoresis. MiniMed Inc. (Sylmar, Calif.) has developed and received FDA approval of an invasive glucose sensor which may be used to monitor glucose continuously for up to three days.

Provided here is a reliable and reduced pain or essentially pain-free approach to frequent glucose monitoring, or for monitoring of any blood metabolite. The use of very small samples, microliter or less, combined with a sensitive and reliable chemical test for the metabolite in an automated device allows for metabolite monitoring with convenience, comfort and reduced pain. The automation of the glucose testing offers an inherent psychological advantage in that the occurrence of the testing is essentially unknown to the user. Automation offers a further advantage in that a specific program can be applied for frequent testing based on the user's life style. With the present invention, a large number; for example 120, of blood tests can be provided per unit, thus allowing frequent testing for up to a month period. Furthermore, miniaturization allows for the design of a small device that can be in the shape of, e.g., a "watch", allowing for portability and unusual convenience.

SUMMARY OF THE INVENTION

The invention provides an analyte monitoring device having a housing, the device comprising: a plurality of needles, each having a tip, a retracted position, a position wherein the tip is extended from the housing a distance adapted to pierce skin; an electrically or spring powered needle pushing apparatus movable to separately engage each of the needles to move each from the retracted position to the extended position; an energy source located within the housing; a plurality of analysis sites comprising an analysis preparation, each adapted to receive liquid from the needles to wet the analysis preparation; one or more light sources adapted to direct light at the analysis sites; one or more light detectors adapted to receive light from the analysis sites; and a processor.

The invention further provides an analyte monitoring device having a housing, the device comprising: (a) a plurality of needles, each having a tip, a retracted position, a position wherein the tip is extended from the housing a distance adapted to pierce skin; (b) an electrically or spring powered needle pushing apparatus movable to separately engage each of the needles to move each from the retracted position to the extended position; (c) an energy source located within the housing; (d) a plurality of evacuated sites, each adapted to engage an associated needle during or following needle movement to apply the vacuum to the needle while it is in an extended position; and (e) a processor.

An analyte monitoring device having a housing, the device comprising: one or more needles, each having a tip, a retracted position, a position wherein the tip is extended from the housing a distance adapted to pierce skin; and a light source fixed to the housing aligned to heat a tissue aligned to intercept the extended positions of the needles.

DETAILED DESCRIPTION OF THE INVENTION

Figure 1:
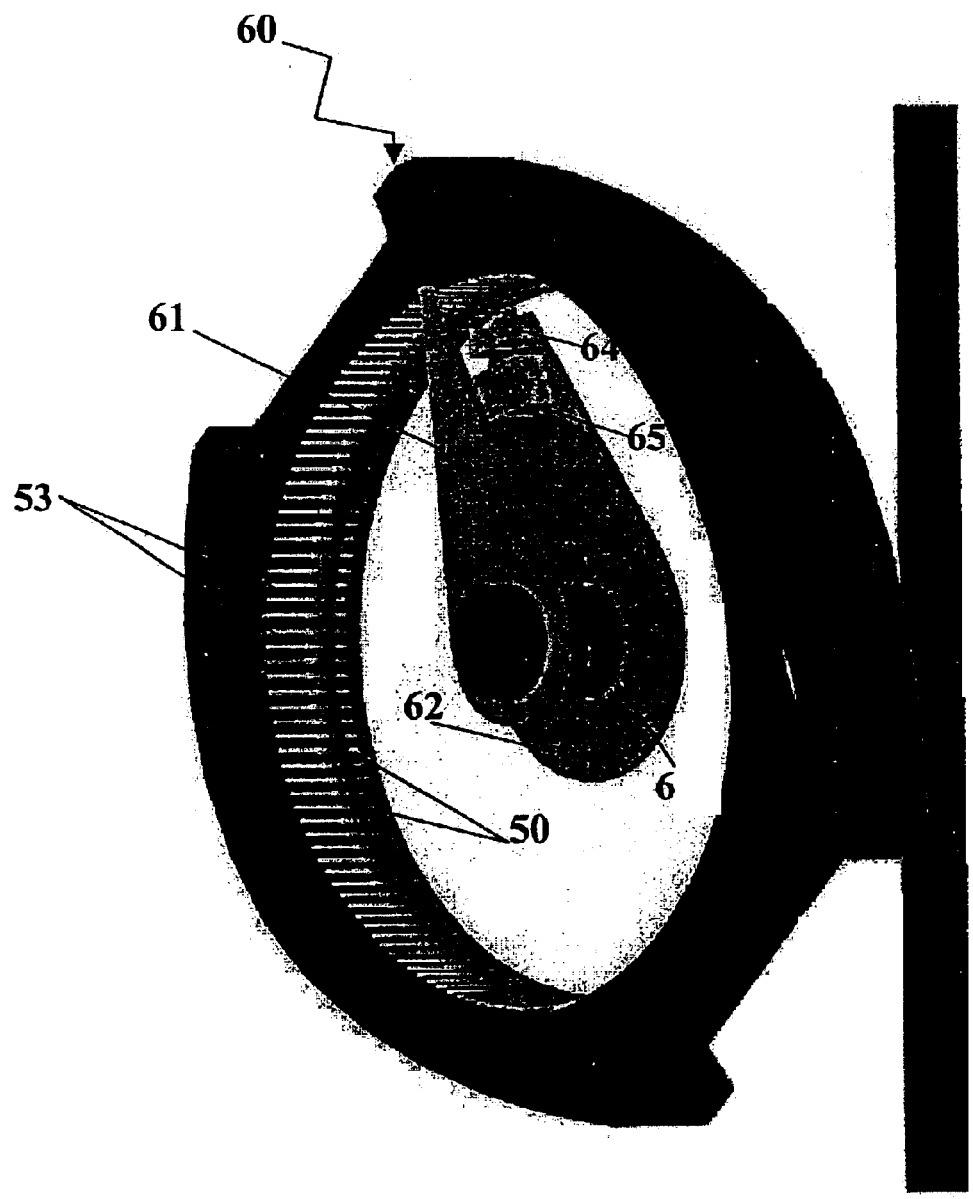
FIG. 1 displays an analyte monitoring device of the invention.

FIG. 1 shows an interior view of a relatively small analyte monitoring device which can be worn strapped or taped to an appropriate tissue from which a biological fluid can be drawn via relatively short, small diameter needles for analysis. The device can be, for example, just over two inches in diameter.

Monitoring device 60 contains a plurality of needles 53, in this case sufficient to conduct a number of analyses (e.g., three to twenty-four) on each of a number of days (e.g., twenty, or forty, or more). The needles are associated with chambers 50 in which, in this embodiment, the analyses are conducted. Such chambers are optionally windowed. Axle 63 rotates platform 62 and arm 61 to align the arm with a needle 53 and the detector 64 on the platform with an associated chamber 50. The detector can contain, for example, a light source and a light detector. The light detected can be used to calculate an absorbance for sample in the chamber 50 (where the light path is reflected back to the detector), or a fluorescence from the sample. A stepper motor, wound spring with appropriate gearing, Geneva mechanism (producing intermittent rotary motion) with a DC motor, or the like can be used to move the platform and arm relative to the respective chamber and needle. A processor 65 accepts data from the detector. In some embodiments, the processor processes the data to derive normalized values, or monitors and controls the positioning of the moving parts of the monitoring device. Where the illustrated ring of chambers is located, for example, one inch from the center of rotation of the arm, they will be located on a circumference of just under 160 mm.

The circular format illustrated in FIG. 1 provides a convenient format, but other formats can be used. For example, detectors can be provided with solid state LEDs and charge-coupled devices (CCDs), such that one or more light sources, and one or more pixels of a CCD can be permanently aligned with each operative chamber, so that control of detector operations is electronic. In other words, the light sources can be serially operated as necessary, and the serial draining of the charge collected in the appropriate CCD can be used to isolate the charges collected in currently operative pixels. One of ordinary skill will also note that all (or a significant subset) of the light sources can be operated, with detector site particularity derived from analyzing the appropriate detectors. However, even when using the differential excitation/emission wavelengths used in fluorescence detection, it is preferable to limit possible sources of cross-talk or electronic noise. Needle movement can be accomplished by a robotic device movable from location to location on x-y oriented cables, or by permanently assigned devices such as electromagnetically operated solenoids.

Figure 2A:
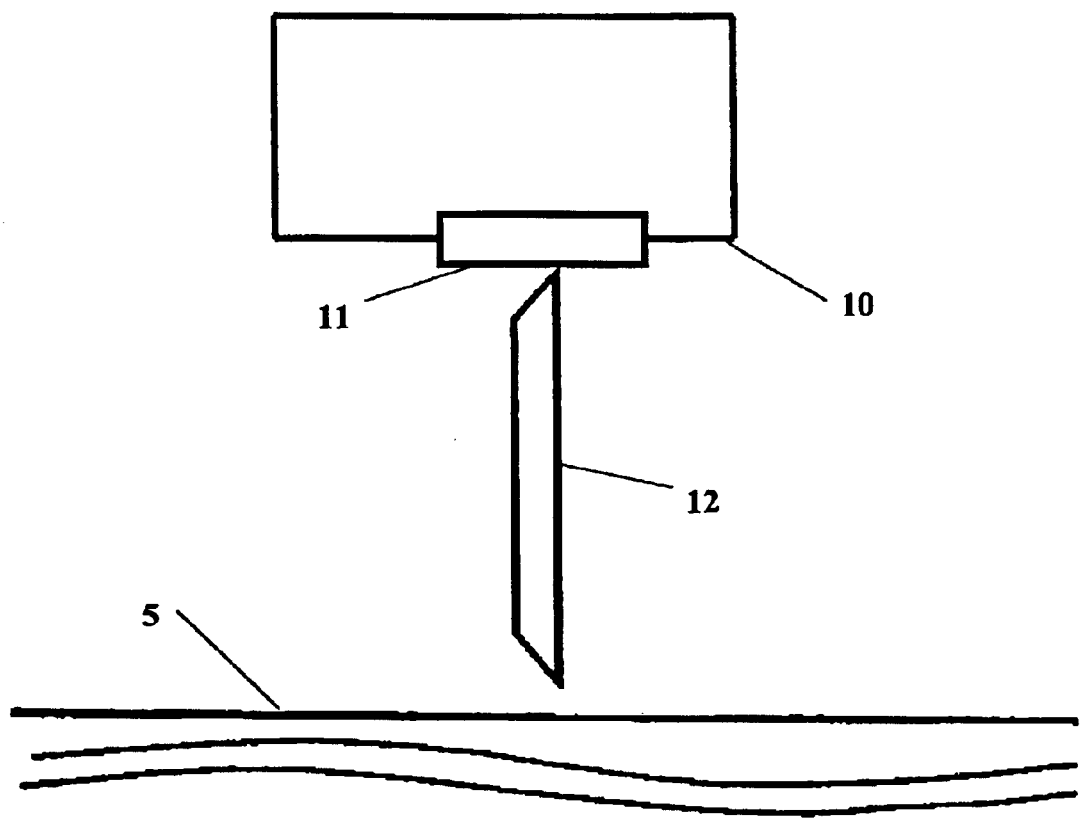
FIGS. 2A-2C schematically shows the operation of one analyte monitoring device of the invention.
Figure 2B:
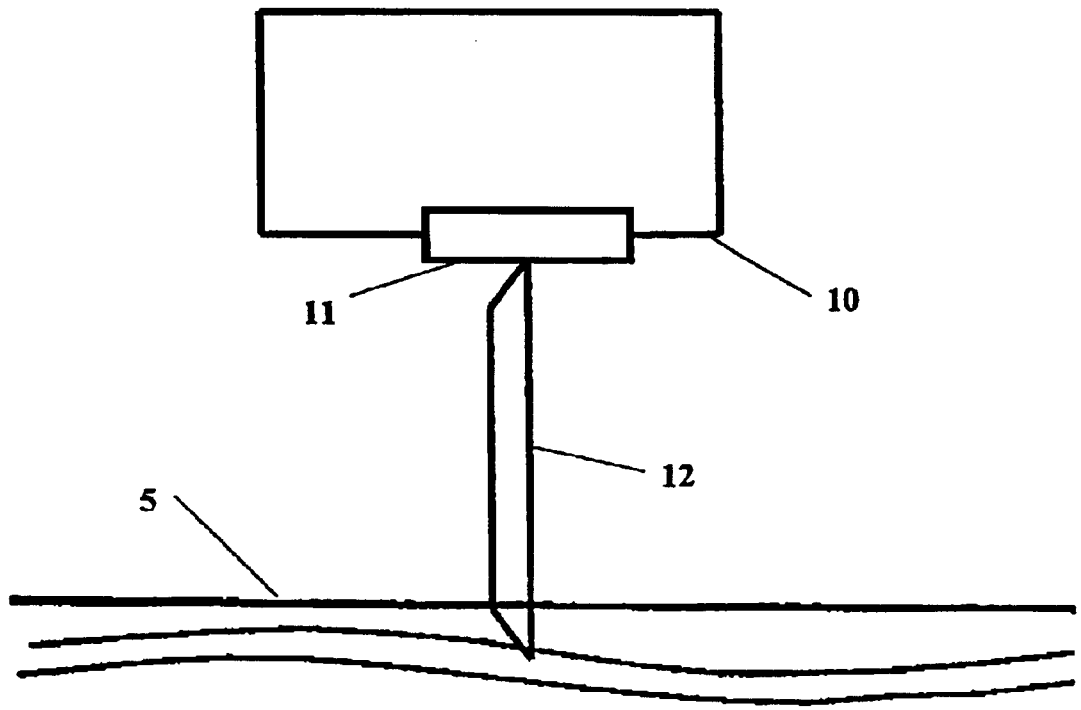
Figure 2C:
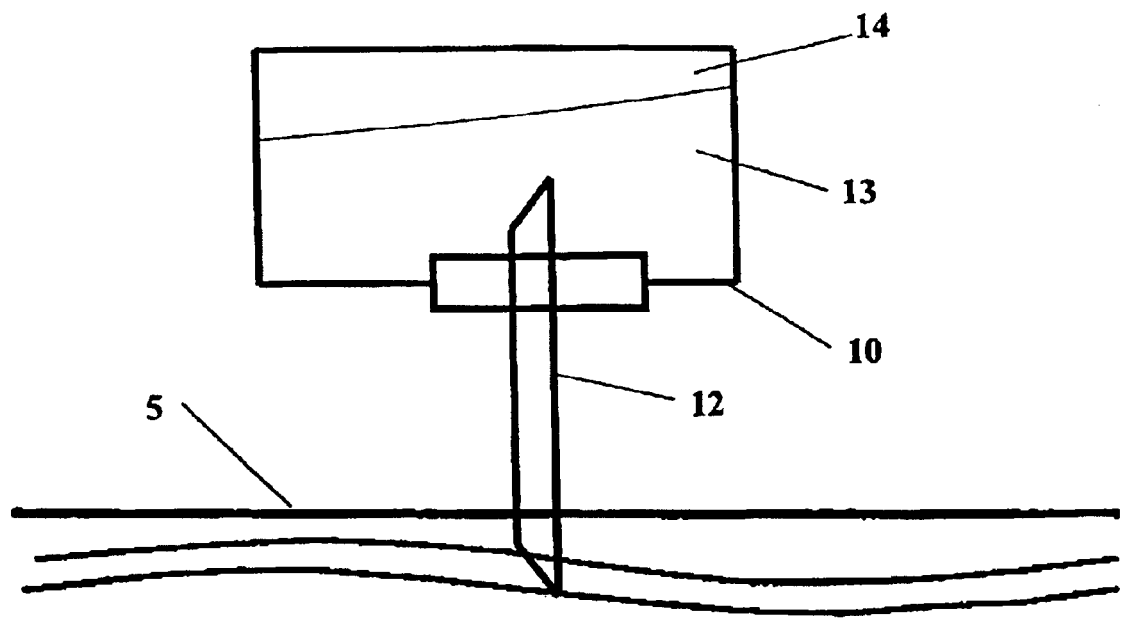

FIGS. 2A-C illustrates the operation of an embodiment of the monitoring device. Chamber 10 is separated from needle 12 by septum 11. After the needle pierces skin 5 (FIG. 2B), the other end of the needle pierces the septum. Chamber 10 can be packaged in vacuum, such that the vacuum provides a drawing force to quickly fill the chamber with fluid 13 drawn from the subject. The increase in filling speed provided by the vacuum helps further assure that no analytical reagents in the chamber will migrate to the patient. The fluid is typically blood or interstitial fluid (ISF). As illustrated, both the needle and the chamber move relative to the skin in this embodiment.

Figure 3A:
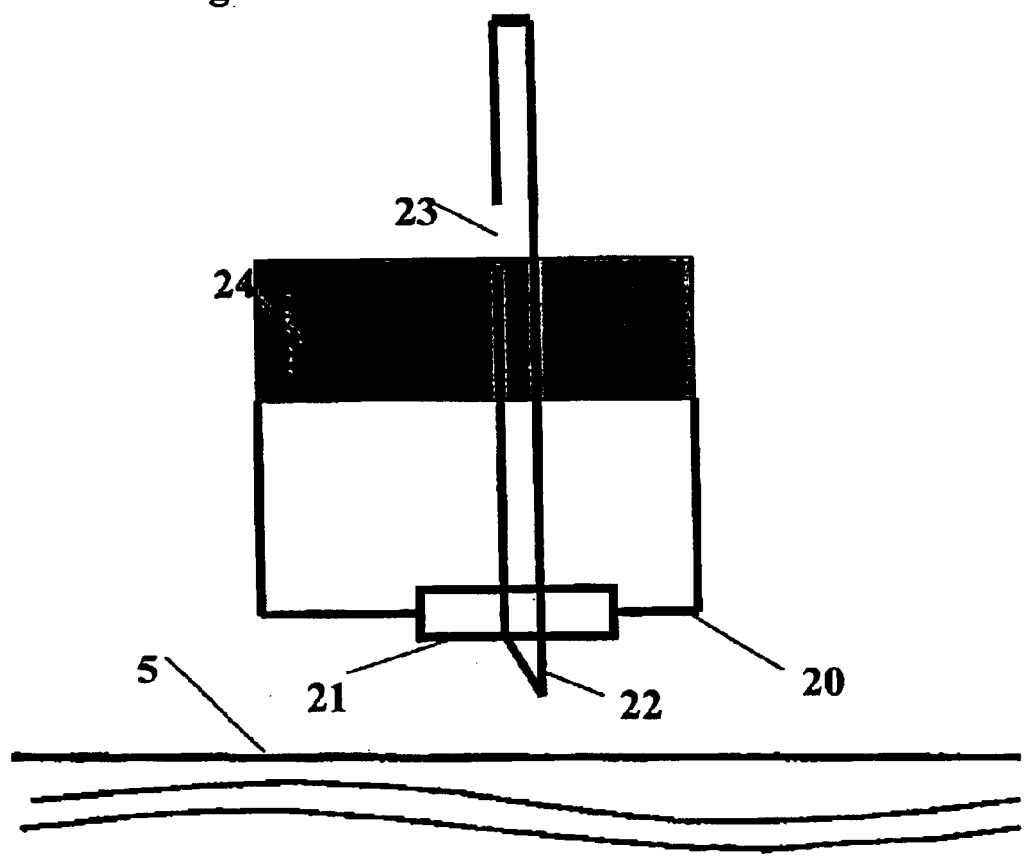
FIGS. 3A-3C shows the operation of another analyte monitoring device of the invention.
Figure 3B:
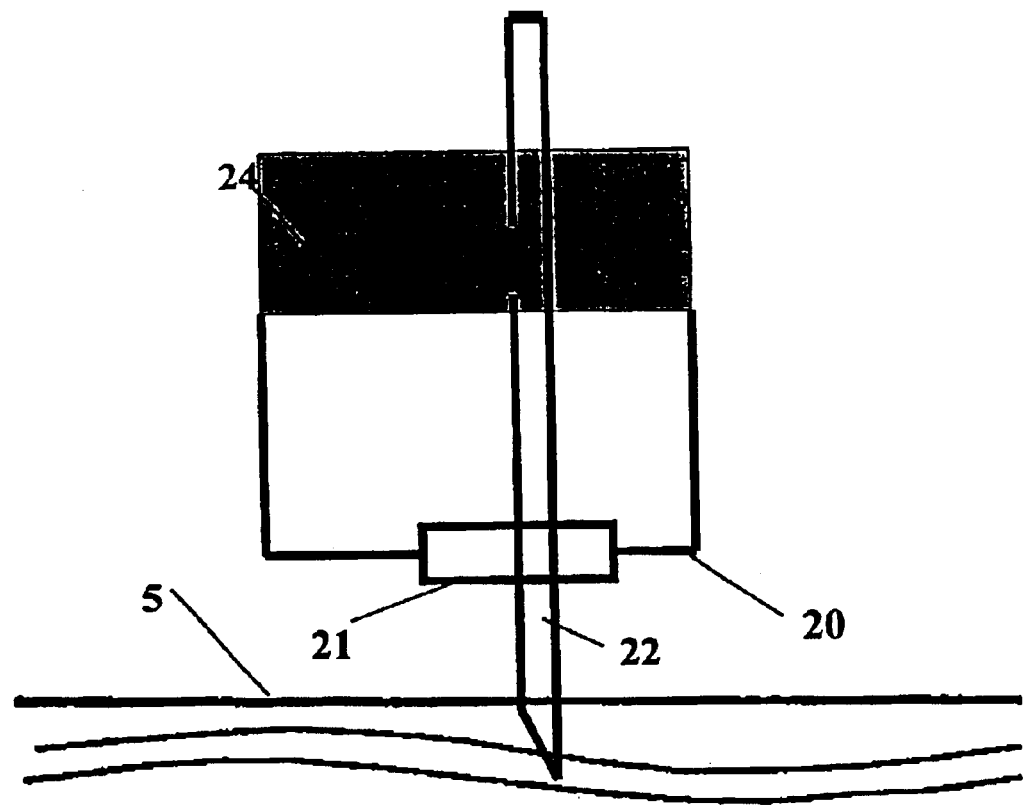
Figure 3C:
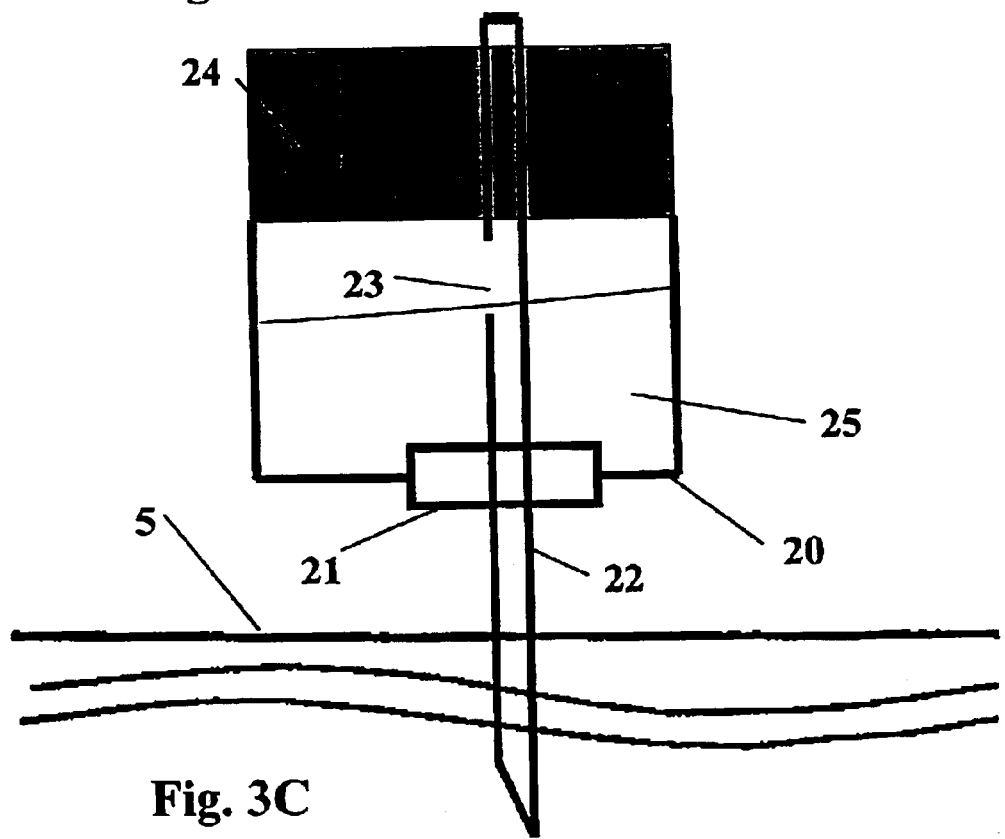

FIGS. 3A-C illustrates the operation of another embodiment of the monitoring device. Chamber 20 is isolated from atmosphere by first septum 21 and second (thick) septum 24. Needle 22 has a side port 23. As illustrated, insertion of the needle into skin 5 brings side port 23 into communication with a vacuum in chamber 20, which vacuum serves to pull fluid 25 into the chamber. The needle is sized, and the side port positioned so that the side port does not open to the chamber until the needle is inserted in the subject. The vacuum used in these embodiments is particularly useful where one seeks to draw blood, as the acceleration in drawing time provided by the vacuum avoids interference from blood coagulation. Nonetheless, vacuum is not required for operation of the invention. Note that the device of FIG. 3 can be used with a second septum, or a thicker first septum 21 to isolate the needle prior to use. After use, the needle is retracted to its original position. In this illustrative embodiment, only the needle moves relative to the skin.

Figure 4A:
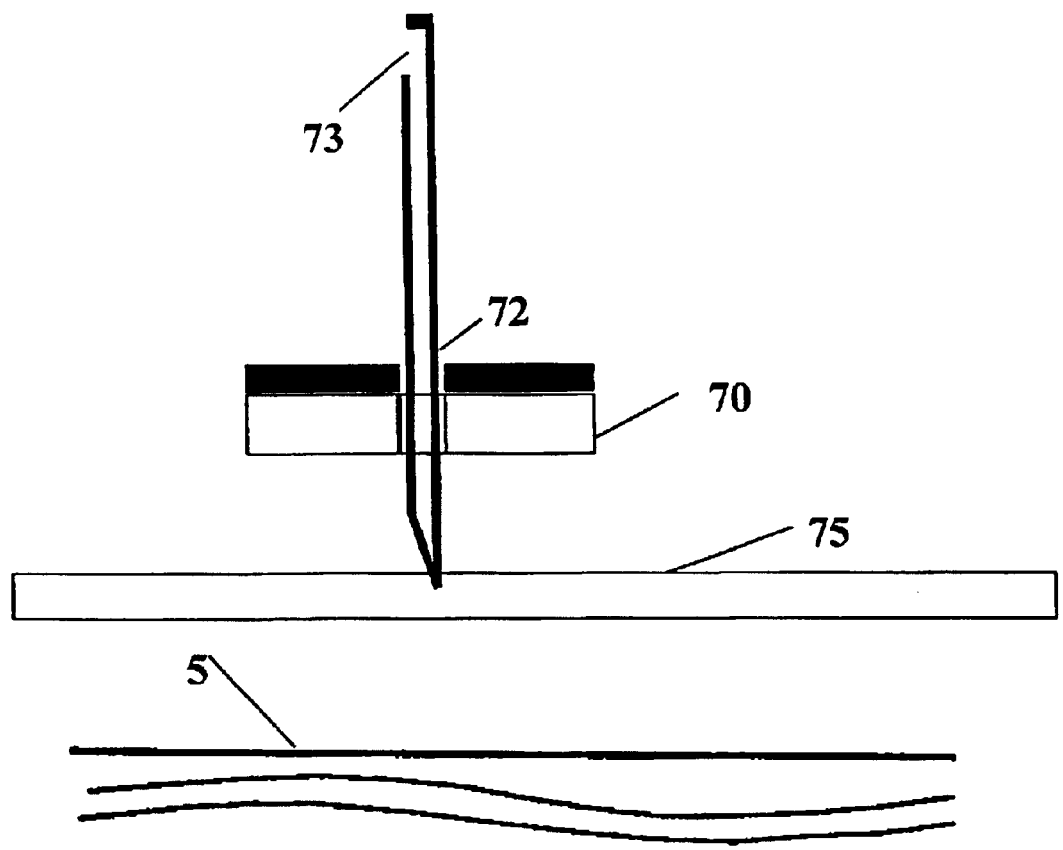
FIGS. 4A-4B shows the operation of an analyte monitoring device of the invention.
Figure 4B:
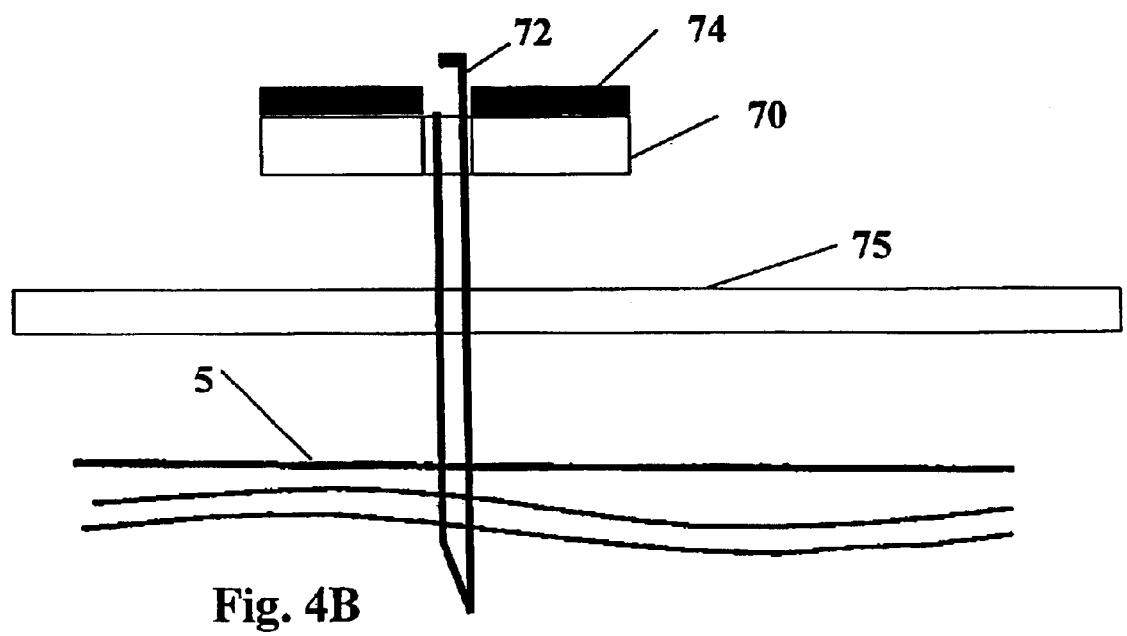

FIGS. 4A-B illustrates the operation of another embodiment of the monitoring device. The needle 72 is actuated through a hole in platform 70, on which platform is located a support 74 (which can be a membrane). When the needle is actuated, it pierces protective membrane/septum 75 and then the skin 5 of the subject. When fully actuated, a port 73 of the needle provides contact for primarily capillary flow from the subject to the support 74. In one embodiment, the support is a membrane on which the reagents needed to drive the analytical reaction have been deposited. Since the reaction volume is typically small, such as 300 nL or less, the reaction can occur primarily within the pores of the membrane. As discussed in U.S. Pat. No. 6,118,126, and in WO 99/23492, appropriate membranes, can be fabricated to provide sufficient amounts of fluorophors in the pores with appropriate proximity to the surface, thereby markedly enhancing fluorescence detected from the fluorophors. The fluorescence enhancement applies where the detector is aligned with backscatter from the excitation light source.

Figure 5:
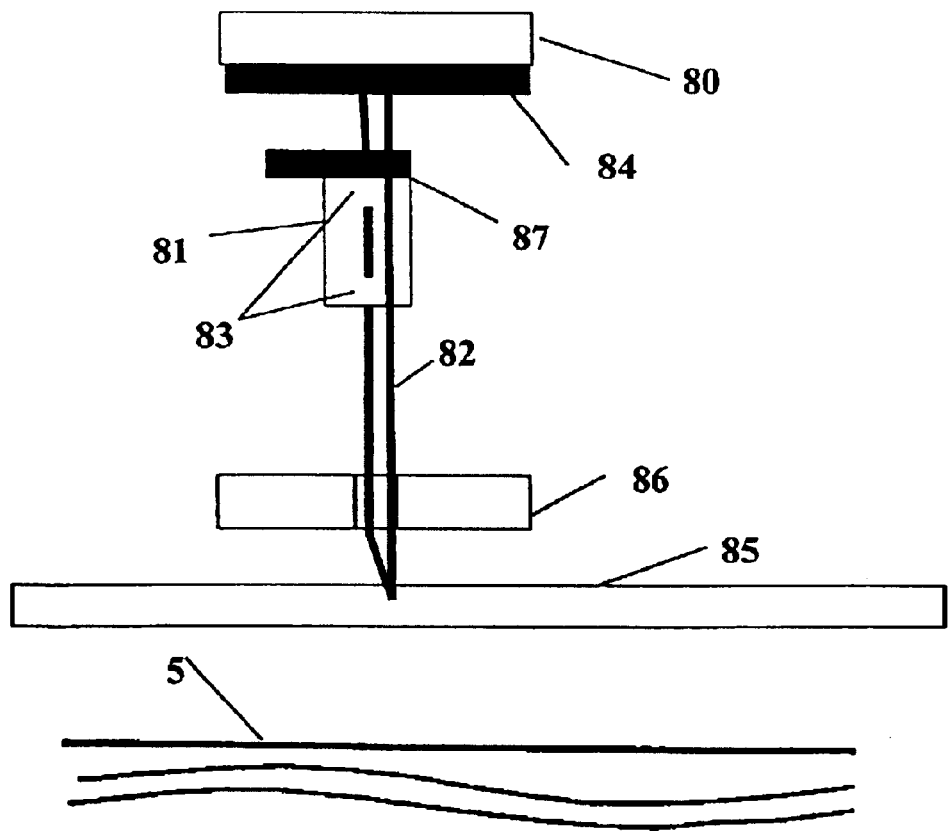
FIG. 5 shows an additional analyte monitoring device of the invention.

FIG. 5 illustrates a further embodiment of the monitoring device. The needle 82 is supported by bracket 86, which guides it toward protective membrane/septum 85 and then the skin S of the subject. The needle is actuated by engaging actuating bar 87, which is illustrated as sitting over reservoir 81. The reservoir serves in this case as a means of drawing a greater volume of fluid through ports 83. Note that preferred needles are of narrow inner and outer diameter, which means that the volume drawn by the needles by capillary action will typically be small, such that the illustrated reservoir can serve to increase that volume. In this embodiment, when the needle is actuated, liquid is drawn by capillary action. Upon removal of the actuating force, the needle retracts (see discussion below) and its upper opening contacts porous support 84, which is supported by platform 80.

Figure 6:
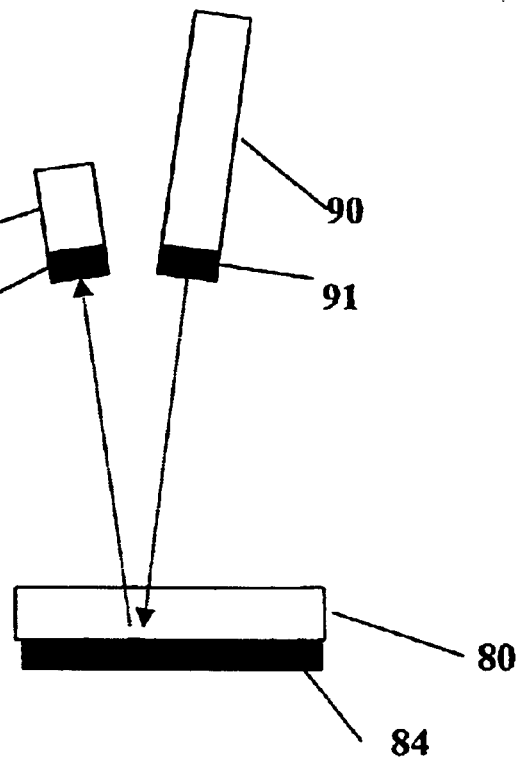
FIG. 6 shows an optical analytic device that can be used in the invention.

The chambers in which the analytical reactions occur, or the platforms on which analytical reaction support reside can be translucent to the wavelengths of light used in the analysis. For example, the platform 80 illustrated in FIG. 5 can be translucent. Thus, as illustrated in FIG. 6, a light source 90 with filter 91 can direct light to support 84 through platform 80, and reflected or emitted light can be collected along a pathway through the platform leading to filter 93 and detector 92. Note that even in this embodiment one can take advantage of the surface effects enhancing fluorescence. The depth of porous support 84, or its porosity distal from the support-platform interface, can be adjusted such that the bulk of the fluorophors will be generated within pores sufficiently adjacent to the interface to provide a useful enhancement in measured fluorescence. For example, the depth at which e.g. $\geq 90\%$ of the fluorophors will reside at the detection stage can be no greater than about 80 microns, or no greater than about 40, 20 or 10 microns.

Note that in the embodiment of FIG. 5, used as illustrated in FIG. 6, the bottom surface of support 84 can be used to isolate cells such as red blood cells away from the portion of the support on which the analytical chemistry and detection shall be conducted. For example, if support 84 is a membrane, the pore size can be selected to exclude the cells. Even with relatively open pores in a porous support, it is anticipated that the cells will not migrate through the support to the support-platform interface that in some embodiments is more important to the analytical determination.

Figure 7A:
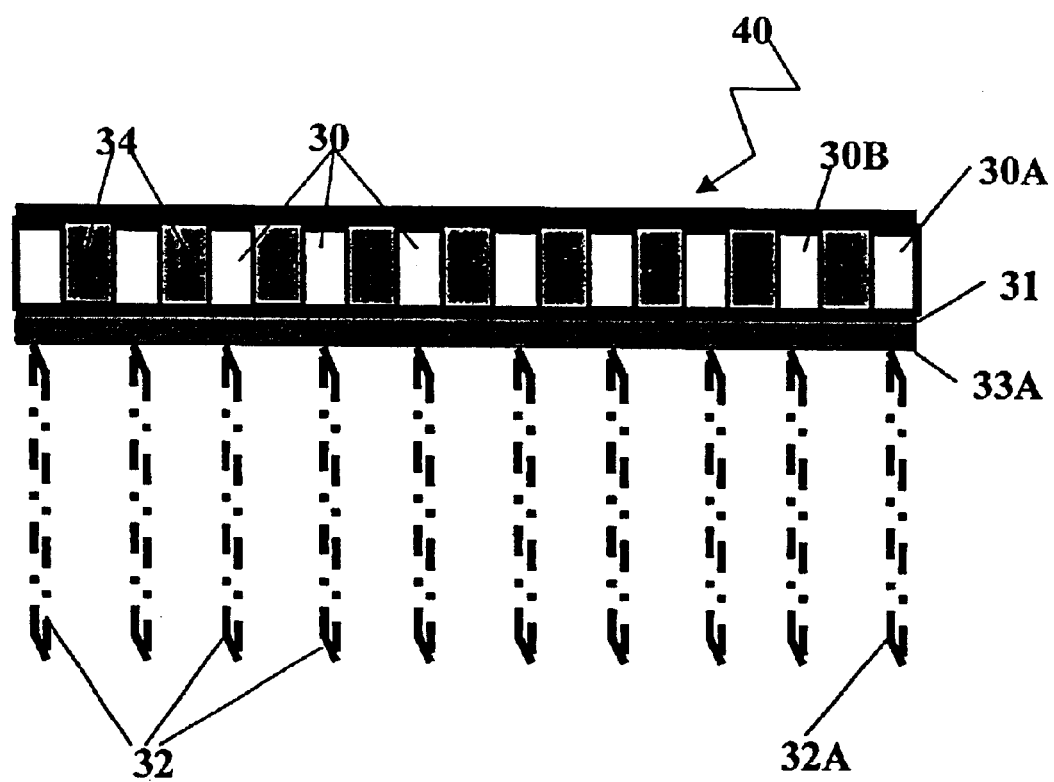
FIGS. 7A-7F schematically shows the operation of one analyte monitoring device of the invention.
Figure 7B:
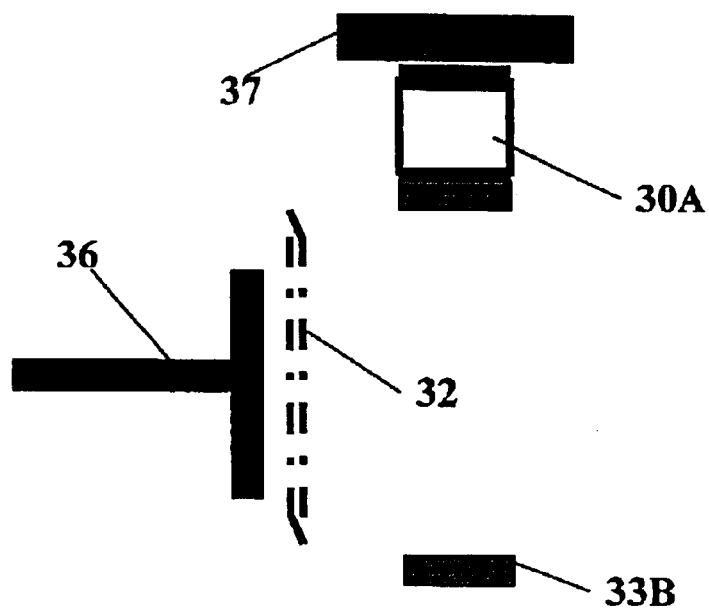
Figure 7C:
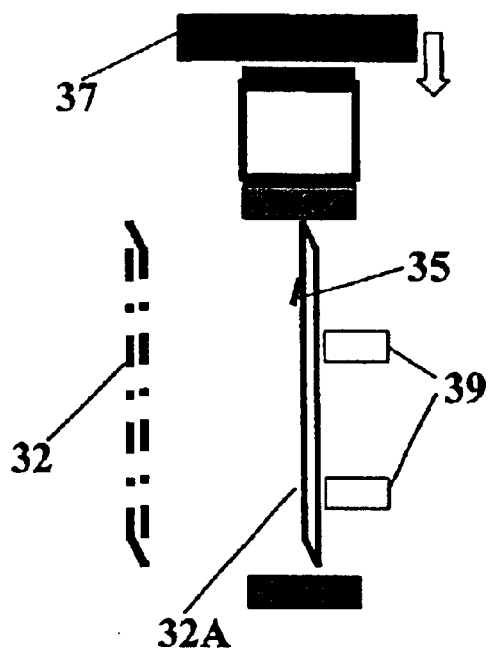
Figure 7D:
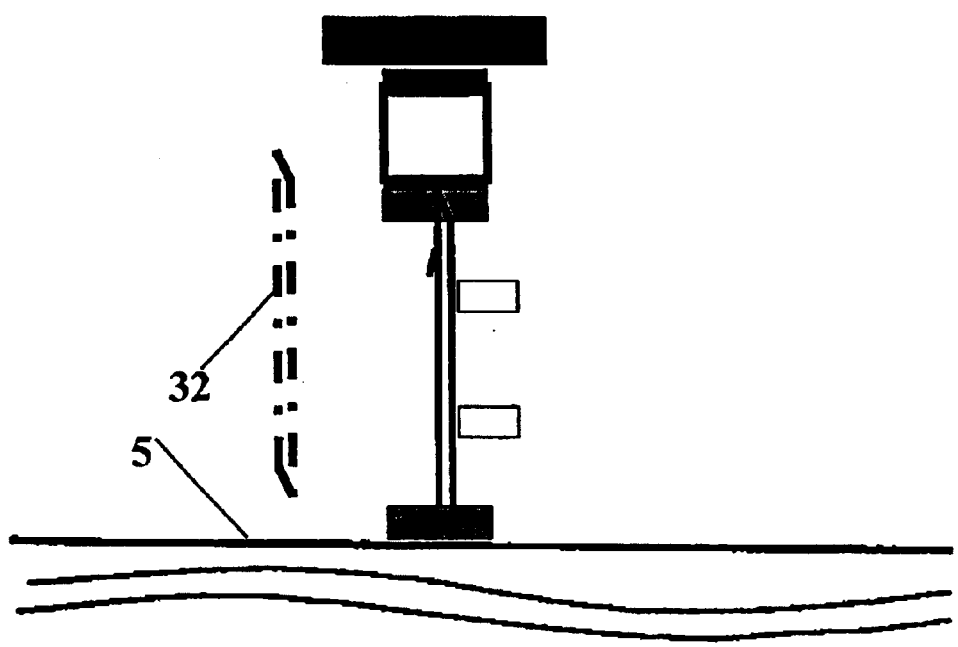
Figure 7E:
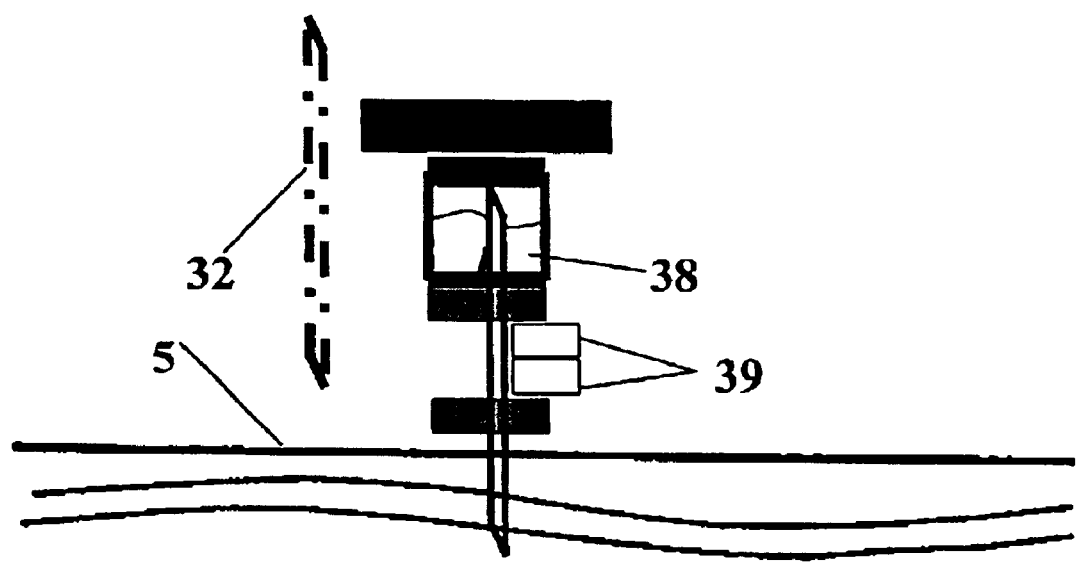
Figure 7F:
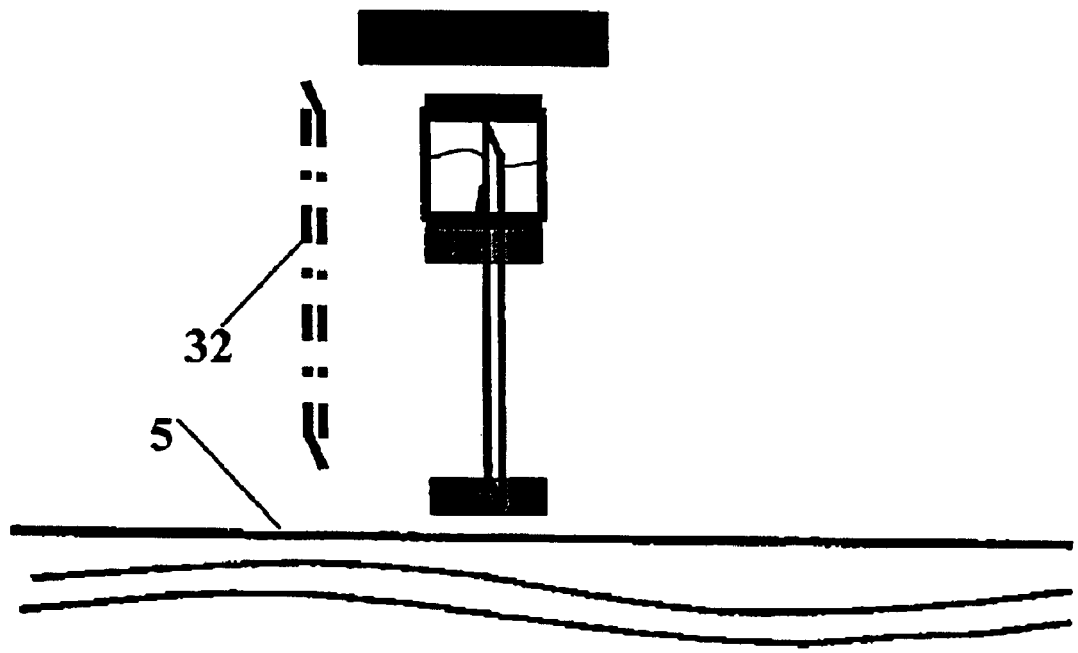

In another embodiment illustrated in FIG. 7A-F, the monitoring device has a tray 40 of chambers 30, such as more specifically identified chambers 30A, 30B, etc., separated by spacers, supports 34. The chambers have associated needles 32, which are indicated in FIG. 7A in hashed lines as they are initially aligned before or behind the tray 40. The chambers are enclosed below by a septum layer 31. The septum layer can be thick to assure no loss of vacuum in the chambers during needle puncture, as here illustrated by a second septum layer 33A. FIG. 7B shows an end view of a cut-out of chamber 30A, together with associated needle 32A. A needle actuator 36, which can be specific to needle 32A, or which can be robotically or rotatably aligned with the appropriate needle as needed. The needle is pushed by actuator 36 until it locks into place, for example into slots in floating alignment brackets 39. Needle 32A can be provided with a bevel 35. Tray actuator 37 can move in the direction indicated by the arrow to engage the ends of the needle 32A in second septum 33A and third septum 33B. The tray actuator also serves as a vertical needle actuator. Further movement of the tray actuator causes the needle to pierce the skin 5 and the chamber 30A, while floating brackets 39 compress to allow for movement. In some embodiments, an initial vacuum in chamber 30A helps fill the chamber with biological fluid 38. The bevel 35 can act to help bring the needle out of the subject when the actuating force is removed.

As illustrated, a large number of chambers can be formed in a single piece of material. The portion of the chambers illustrated in FIG. 7A forming the top wall of the chambers, for example, can be formed of the same single piece that in this embodiment forms the cavities. It can also be formed separately and sealed to the supports 34. Of course, the septum 31 and second septum 33A are formed separately. However, as illustrated, septa acting for a number of chambers are preferably formed of one piece of material.

Figure 8A:
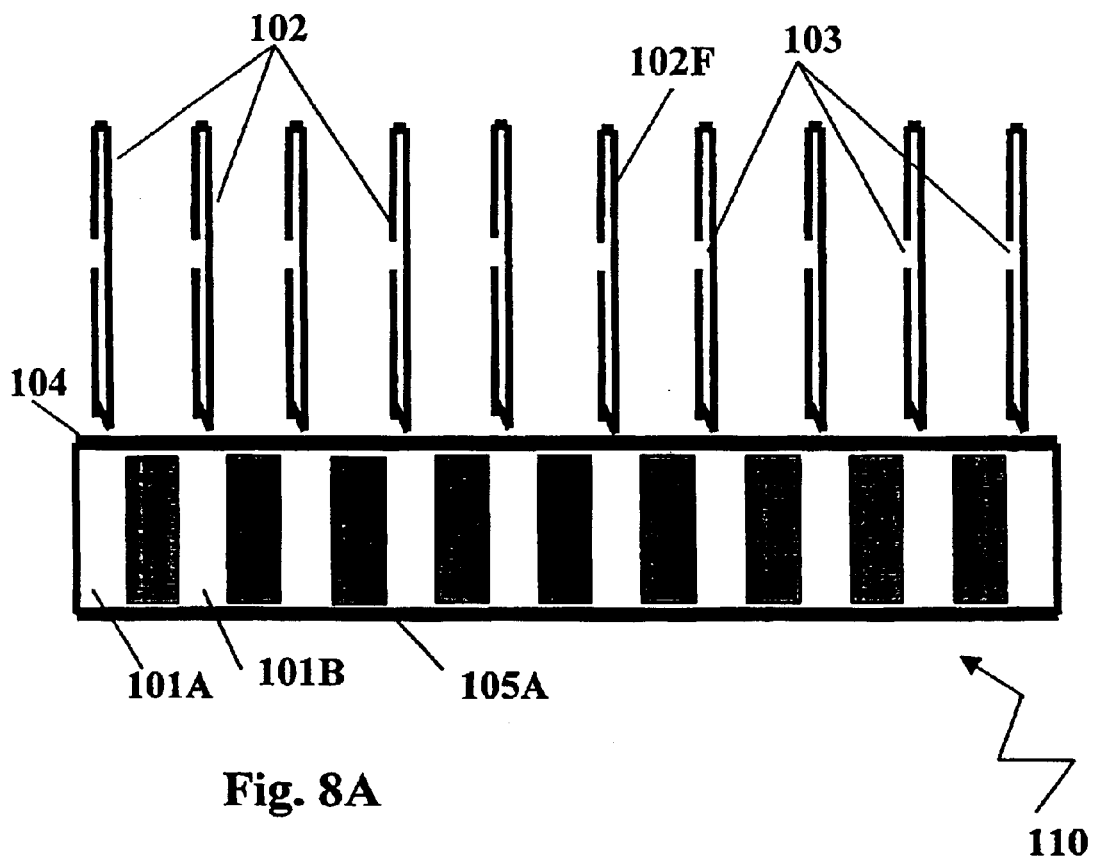
FIGS. 8A-8D shows the operation of another analyte monitoring device of the invention.
Figure 8B:
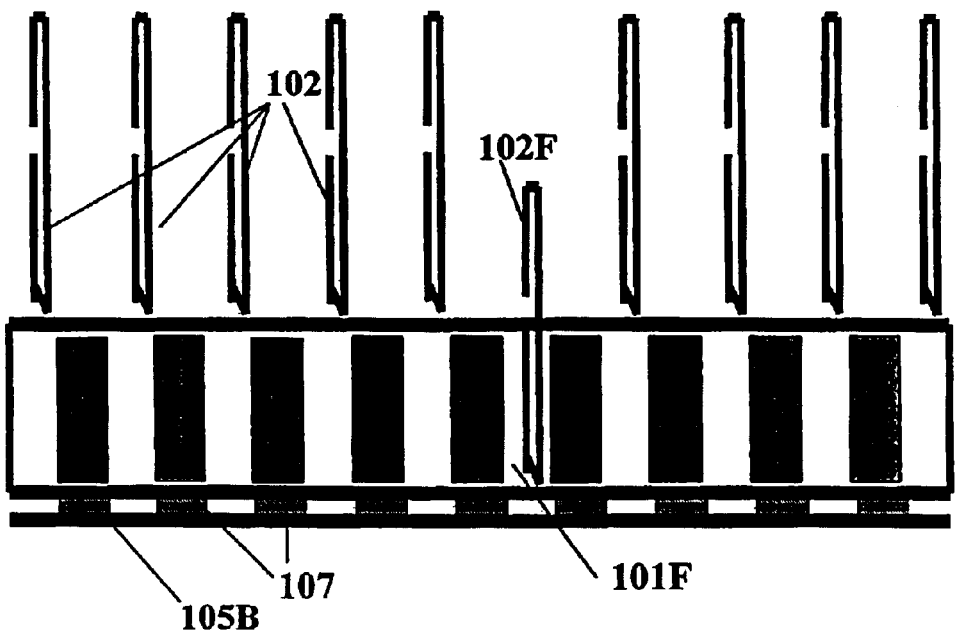
Figure 8C:
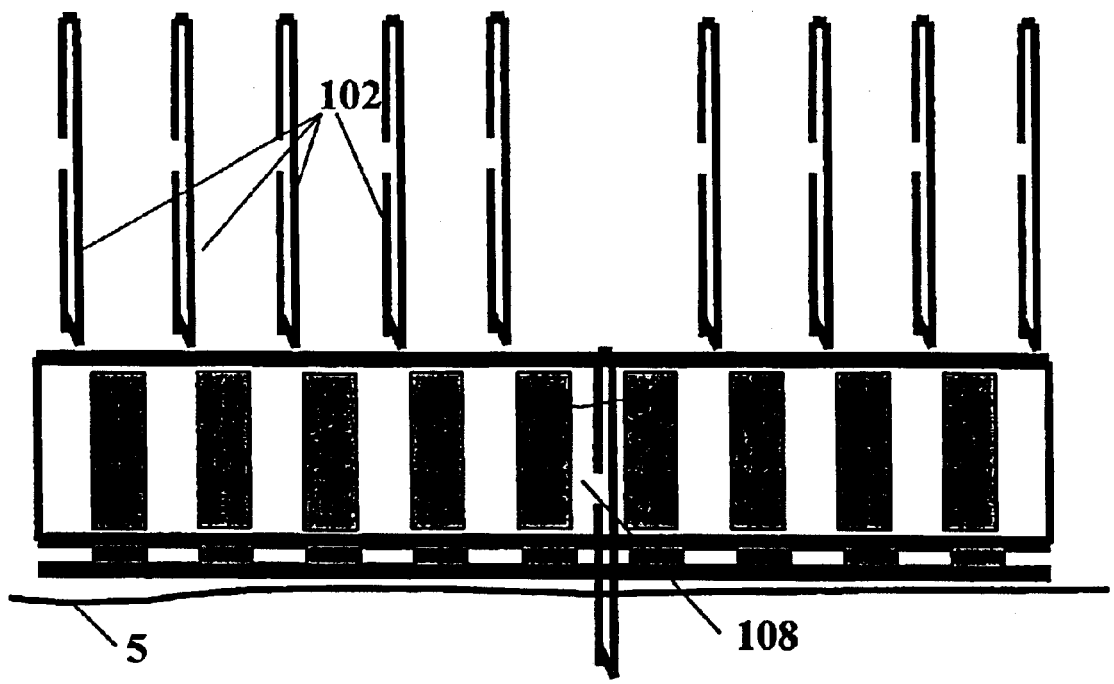
Figure 8D:
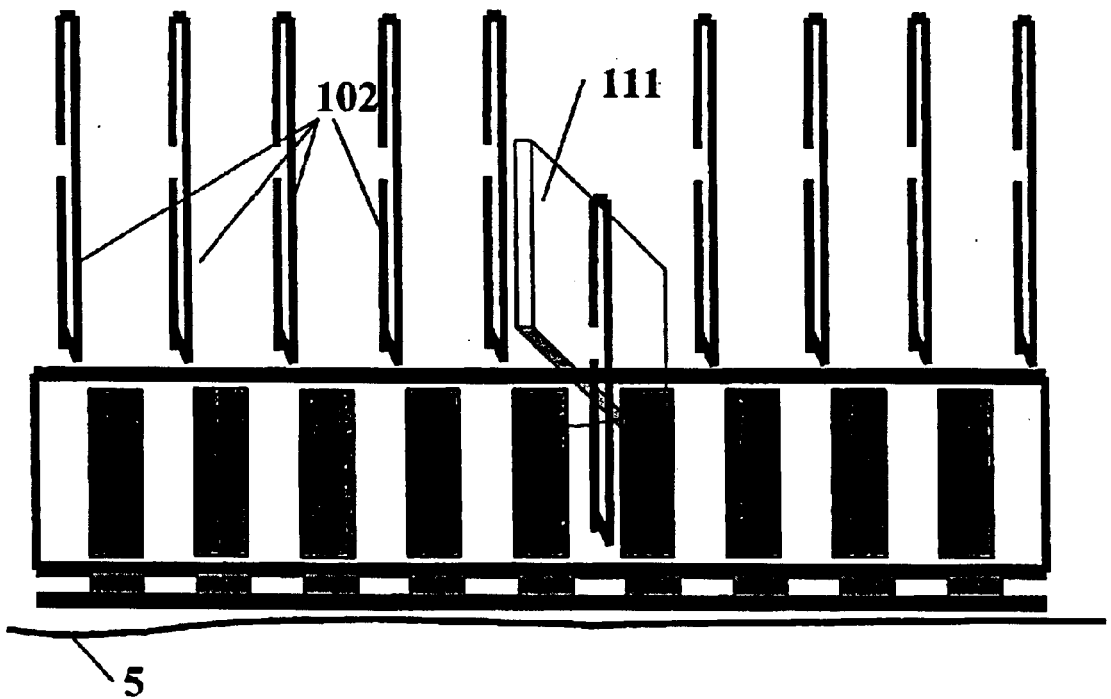

In another embodiment illustrated in FIG. 8A, tray 110 has chambers 101, such as specific chambers 101A, 101B, etc., enclosed top and bottom by first septum 104 and second septum 105A, respectively. Needles 102 have side ports 103. In FIG. 8B, needle 102F is partially actuated so that first septum 104 is breached, but second septum 105A is not. At this stage, a vacuum in the housing in which the needles are stored equilibrates with the interior of chamber 101F. A pump can be actuated as needed to create, maintain or supplement the vacuum in the housing. Care is taken to preserve the vacuum while the needle is further actuated by use of a thicker second septum 105A or the use of a third septum 105B supplemented by an evacuated space between the second and third septa. Spacers 107 support the third septum. Vacuum is not substantially compromised while the needle tip relatively quickly travels to pierce skin 5, leading to biological fluid 108 filling chamber 101F. In one embodiment, fluid 108 can then be transferred to support 111 by capillary action, as illustrated in FIG. 5D. As previously, optical measurements can be made from either face of the support, with measurement on the reverse face allowing the support to act as a filter removing cells from the area generating the spectroscopic data.

Chambers

Chambers can be made of a number of materials which have proven stable to, for example, blood analysis samples and reagents, and which preferably are compatible with one or more sterilization processes. Such materials include suitable plastics, glass, silicon, quartz and the like. Suitable plastics include, for example, polycarbonate, polysulfone, acrylic (e.g. polymethyl methacrylate), polystyrene, styrenic copolymers such as NAS copolymer of polystyrene and acrylic, styrene acrylonitrile copolymers (e.g., SAN), polyurethane, polyethylene, polyethylene terephthalate and 4-methyl-1-pentene (e.g., TPX) plastics. See, "Guide to Engineering Thermoplastics," in *Medical Devices and Diagnostic Industry*, April, 1995; and *The Handbook of Plastic Optics*, $2^{nd}$ Ed., U.S. Precision Lens, 1983. Since it is frequently desirable to make the analytical spectroscopic measurements of material in the chamber, a simplified method of providing a suitable optical window is to manufacture the chambers of materials that transmit light of the wavelengths required for the analysis. Since the wavelengths needed for many of the analyses are sufficiently high, a number of plastics are suitable, including those identified above.

With plastics, for example, structures can be formed by injection molding, casting, machining, and other methods known in the art. Where particularly fine dimensions are needed, LIGA (a German language acronym for lithography, electroplating, and molding) molding, wherein molds are formed by photolithography from relatively thick photoresist layers, can be used. With glass, silicon, and the like, etching techniques, particularly techniques that generate well defined walls, such as reactive ion etching, can be used.

The size of the chambers will typically be small, such as sufficient to draw a small volume such as 5,000 nL, 2,000 nL, 1,000 nL, 500 nL, 300 nL, or less. Note that a 0.67 mm (26 mils) by 0.67 mm by 0.067 mm space provides a volume of about 300 nL. Of course, the size of the space used to draw the desired volume will typically be larger than the volume obtained by the drawing process, as can be established by ordinary experimentation.

The device has for example 32, 64, 96, 128, 160 or more chambers (and associated needles) to provide 1, 2, 3, 4, 5 or more daily samplings over the course of about a month.

Note that where optical detection is conducted from substantially the direction of the light source, a reflective surface (if needed) can be incorporated into the monitoring device, such as on an outside surface of the chamber.

Septa

A septum or protective membrane used in the invention can be made of a polymer, such as a silicone rubber, Teflon (polyperfluoroethylene), polyethylene or an elastomeric film (such as a natural rubber, ABS rubber, or polyurethane elastomer film). In other contexts, greater thicknesses are needed to preserve vacuum in an associated chamber during actuation of the associated needle until the vacuum comes into play in helping draw fluid. A number of factors in selecting the septum will be considered by those of ordinary skill, such as the limitations of the septum-forming method, the flatness of the top surface of a septum as produced by a given method, the hardness of the septum-forming material, the open area to be sealed by the septum, and compatibility with a suitable method of sterilization.

One method of attaching the septum is screen-printing. The printed septum can be made of silicone or another chemically-resistant, resilient material. Preferably, the septum is made of a mixture of (a) a silicone rubber-forming material such as that available under the Sylgard 184™ brand from Dow Corning, Midland, Mich. or MDX4-4210™ also from Dow Corning and (b) an inert filler, such as the amorphous fumed silicon sold as M-5 grade Cab-o-sil™ (Cabot Corp., Boston, Mass.). Sylgard 184 and MDX4-4210 are sold in two components. One component is an emulsion containing particles of silicone rubber and a polymerization catalyst and the second component is a preparation of a bi-valent monomer, which monomer serves to crosslink and thereby cure the silicone rubber. Component one of MDX4-4210, i.e. the "elastomer component," is made up of dimethylsiloxane polymer, reinforcing silica, and a platinum catalyst. Component two of MDX4-4210, the "curing agent," also contains dimethylsiloxane polymer, in addition to a polymerization inhibitor, and a siloxane crosslinker. The components are generally mixed according to the manufacturer's recommendations. For example, for MDX4-4210, ten parts by weight of emulsion, i.e. elastomer, are mixed with one part of monomer solution, i.e. curing agent.

As examples of the use of inert fillers, about 7.5% by weight of M-5 grade Cab-o-sil can be added to the Sylgard 184, or about 2–3% by weight of M-5 grade Cab-o-sil can be added to the MDX4-4210. Filler can serve to thicken the pre-polymerized composition to improve its screen printing properties. Septum-forming materials can generally be cured at room temperature, or curing, can be accelerated, for example, with heat. Prior to curing, the septum-forming material is capable of flow, though generally viscous flow, which flow is sufficient to facilitate the screen printing process. The septum-forming material is also sufficiently adhesive to adhere either to the plate to which it will be applied or to an underlying first layer of septum-forming material.

In one version of the screen printing process, a first layer of septum-forming material is printed onto the plate and then cured. After this first printing, a second layer of septum-forming material is overlaid on the first, a smooth platen of appropriate shape (generally very flat) is overlaid upon the printed septum-forming material so that a uniform weight is applied to the printed septum-forming material (while taking precautions to prevent destructive adhesions of septum-forming material to the platen such as described further below), and the septum-forming material is cured. The use of two printings of septum-forming material helps form a foundation of septum-forming material prior to the smoothing process conducted after the second printing. To achieve this smoothness and uniform thickness, it is important to apply a sufficiently uniform pressure to the septum during a final curing process. This pressure should be selected to be, for the particular septum-applying process, sufficiently high to create the needed uniformity during the curing process, but not so high as to overly compress cured portions of septum-forming material such that upon release of the pressure these portions re-expand and create a non-uniform seal thickness. A single print process can also be used, and such a single print process is generally preferred since it is simpler and more readily applied to a production process. In a single print process, which is described further below, a platen is applied directly after the first (and only) printing of septum-forming material, and prevented from settling down too far or too unevenly by mechanical stops.

Preferably, the width of each print feature on the screen is uniform, as width non-uniformities increase the probability of a thickness non-uniformity at the end of the process. After printing and processing, the applied septum patterns are broadened. For example, in applications using the two-print process and 6 mil wide pattern on the print screen, an 18 mils wide pattern has been produced.

Because the septum material is applied over openings forming chambers, the initial formation of the gasket is usefully conducted on a flat surface adapted to not adhere the septum-forming material, such as glass treated with a release agent such as silicone oil or a siliconizing agent. A second layer of septum-forming material can be applied, and the septum transferred to the surface on which the cavities are formed while the septum-forming material of the second layer is still sufficiently tacky to adhere.

Needles

An important feature of the invention is the provision of small-scaled needles with sufficient rigidity and durability. The small scale is important to provide the number of analyses in one device needed to substantially ease the burden of conducting numerous analyses over the course of, for example, a week. Small size also reduces the pain associated with piercing the subject's skin. The needles are able to sustain a 0.3 mN force to allow insertion through, for example, a subject's skin.

Preferably, the needles are 8 mils or 200 μm or less in diameter, preferably with an inner diameter of at least about 50% of the outer diameter. Inner diameters of 6 mils (150 μm), 4 mils (100 μm), 2 mils (50 μm) or 1 mil (25 μm) or less are contemplated. The length of the needles is adapted to provide the communication with internal constituents of the monitoring device and sufficient penetration into tissue to obtain the desired biological fluid. Typically, the needles can be 10 mm or less, 4 mm or less, 2 mm or less, or 1 mm or less in length. Where ISF is the targeted biological fluid, the length adapted to penetrate the subject will be sufficiently short to avoid piercing through the dermis, which typically has a depth of 2 to 3 mm.

The needles can be made by small-scaled molding of suitable plastics. One such small-scaled molding technique uses LIGA (German acronym for lithography, electroplating, and molding) to create small-scaled molds. Suitable plastics include polyetheretherketone (PEEK) and polyethersulfone (PES). The polymer can be filled with a reinforcing substance, such as 10–40% filled with glass or carbon fiber.

Plastics can be extruded with outer diameters of, for example, 4 mils (100 μm) or less, and inner diameters of 2 mils (50 μm) or less.

Glass and suitable plastics can be drawn to suitable inner and outer diameters. It should be noted that the inner to outer diameter ratio is maintained during the drawing process. Glass needles can be diamond coated by vapor deposition.

Silicon wafers can be used to form needles by reactive ion etching or other high definition etching techniques. For example, 40:1 height:width ratio features can be created. The needles are formed from the wafer leaving a tab connecting the needles formed from the wafer. The needles are, for example, mechanically separated. The wafer can be etched at an angle to create a beveled needle tip. A sharp tip can also be formed with an initial etch using an anisotropic etching method, such as ethylene diamine/pyrocatecol/water (EDP) or KOH etching.

Alternatively, the needles so formed of silicon can be used as reverse molds to form molds for plastic needles. Or, the wafer can be directly etched to form the molds.

The needles can also be formed of, for example, sapphire ($Al_2O_3$) or quartz. For example, edge-defined methods can be used wherein molten material is contacted with an initial mold which draws up a leading edge by capillary action. Subsequently the mold is drawn upwards, and the sapphire or quartz material crystallizes in a geometry matching the leading edge drawn from the molten material.

Needles can also be of metal. Metallic needles are formed, for example, by drawing needles formed to a larger scale. Electrochemical cutting, for example, can be used to cut the needles while electrochemically removing burrs or other ruff edges. Alternatively, needles can be formed by extrusion and ground to the appropriate shape.

Bevels can also be created by, for example, laser cutting of the needle ends.

Supports

In some embodiments, the assay is conducted on a support on which assay reagents have been previously deposited. The support can be calibrated to wet with a desired volume of fluid sample.

It is believed that an important characteristic for achieving the fluorescence enhancement result described here is the presence of voids on the surface or interior of the material. It is believed that such voids provide "microcavities" or "scatter cells" which contribute to the phenomenon, basically by increasing the pathlength of the excitatory radiate energy, thereby increasing the probability of fluorescence excitation events. It is further believed that the voids should be present in sufficient density to so that the beam of excitatory light sees a uniform density of such microcavities or scatter cells. The material should not absorb light of the excitatory wavelength that is to be used to induce the fluorescence. If broad band light is to be used, then the material should not be absorptive of the portion of the light that is effective to induce the fluorescence. A narrow band of light, or even laser light source, is preferred as the source of excitatory light. It is because of the absorption issue that, when nylon membranes are used, fluorescent reagents that are excited by, for example, He—Ne lasers are preferred over those excited by argon lasers.

It is further believed with many textured materials the enhancement effect is most pronounced when the emissions are collected over a relatively narrow collection surface positioned at and around an axis corresponding to the angle of reflectance for the excitatory light. Preferably, the collection surface covers no more than about the area of a 20° cone extending from the textured surface and symmetrically positioned about the above-described axis. More preferably, the collection surface covers no more than about the area of a 10° or 5° cone. Preferably, the angle of incidence of the excitatory light is substantially 90° relative to the textured surface, such that the collection zone is along the same axis, as illustrated in FIG. 1. "Substantially" 90° in this context refers to an angle which helps maintain at least about 75%, preferably at least 85%, 90% or 95%, of the fluorescence yield available with a 90° angle.

Suitable textured materials include, but are not limited to, nylon, poly(carbonate), poly(vinylidene difluoride) ("PVDF"), and nitrocellulose membranes. Preferably, nylon membranes are used, including commercial nylon membranes, such as those from Pall Corp. (East Hills, N.Y., or particularly, Biosupport Division, Port Washington, N.Y.), Amersham Pharmacia Biotech, Inc. (Piscataway, N.J.) and Cuno Inc. (Meriden, Conn.).

Assay Reagents

The reagents for use in creating a fluorescent signal in response to the analyte are typically enzymes, enzyme cofactors, buffering agents, salts, and stabilizing reagents. The reagents are selected from reagents that can be stored in dry form and dynamically re-hydrate to active form. One common assay design makes use of one or more steps in a biosynthetic or catabolic pathway that generates a reduced form of $NAD^+$ or $NADP^+$ or other electron carrier (e.g., FMN, FAD). The assay can make use of a cascade of enzyme-mediated reactions that generate in excess of one equivalent of reduced electron carrier per analyte equivalent. The reduced electron carrier is used to reduce a fluorophor precursor to create the fluorophor, for example, using diaphorase.

For example, where glucose is the analyte, ATP and glucose kinase can be used to generate glucose-6-phosphate (G6P). An oxidized form of an electron carrier, e.g., $NADP^+$ G6P is then acted on by a 6-phosphogluconate dehydrogenase to generate the reduced form of the electron carrier. The reduced form of the electron carrier and a suitable fluorophor precursor are then acted upon to generate the fluorophor. Such methods are described, for example, in U.S. Pat. No. 5,360,595 (calorimetric strip assay), U.S. Pat. No. 5,302,513 (fluorometric assay using diaphorase) and U.S. Pat. No. 5,912,139.

Buffering agents, if needed, are provided in amounts suitable to stabilize the pH in a range that allows effective action by all the enzymes used in the assay. Similarly, salts, if needed, are provided in amounts determined to support all of the enzymes used. Stabilizing agents, such a glycerol and inert polymers such as PEG are provided as empirically determined to be useful.

Dyes which have enhanced fluorescence in a reduced state and which have been shown or are thought to be useful with a diaphorase include salts of 7-hydroxy-3H-phenoxazin-3-one (Resazurin), neutral red, 4',6-diamidino-2-phenylindole (DAPI), bisbensimide (Hoechst 33258), and the like.

The assay agents can be provided on a polymer support that dissolves or disperses on hydration. As discussed elsewhere, the assays can be conducted on a more stable support on which the assay agents are deposited. Deposition techniques will be recognized by those of ordinary skill. These include drying from liquid form and the method described in U.S. Pat. No. 6,045,753 (Loewy et al.)

Optical Detection Elements

Individually addressable LEDs can be constructed by packaging individual LEDs of suitable dimensions on a circuit board allowing the individual illumination either of each LED or a subset of the LEDs. For example, the semiconductor laser diodes (visible and infrared wavelengths) available from Opto Power Corporation (Tucson, Ariz.) or SDL, Inc. (San Jose, Calif.) can be so packaged. Alternatively, such LEDs with emitter center-to-center dimensions of 14 micrometers or 100 micrometers are available pre-packaged in multiples of 4 from SDL, Inc. For such relatively closely spaced light emitters, optics are generally used to direct the individual beams towards the more widely spaced-apart detection sites. The closely packed emitters have advantages in cost and simplicity of the housing requirements. Where each emitter will be directly aligned with a detection site, preferably the center-to-center dimension used in the present application ranges from about 1 mm to about 20 mm. In various embodiments, preferred ranges are from about 1 mm to about 20 mm, from about 1 mm to about 10 mm, or from about 1 mm to about 5 mm.

Detector arrays can be, for example, a charge coupled device (CCD, such as that available from DALSA, Inc. (Easton Conn.), Sarnoff Corporation (Princeton, N.J.) or Princeton Instruments (Trenton, N.J.)), an intensified CCD array (such as that available from Princeton Instruments, Hamamatsu Corp. (Bridgewater, N.J.) or Photometrics Ltd. of Tucson, Ark.), a focal plane array (such as that available from Scientific Imaging Technologies, Inc. (Beaverton, Oreg.), Eastman Kodak Co., Inc. (Rochester, N.Y.) or Sarnoff Corporation), a photodiode array (such as that available from Reticon Corp. (Sunnyvale, Calif.), Sensors Unlimited, Inc. (Princeton, N.J.) or Hamamatsu) or photodetector array (such as that available from FLIR Systems Inc. (Portland, Oreg.), Loral Corp. (New York, N.Y.), or Hughes Electronic Corp. (Los Angeles, Calif.)).

Controller

The monitoring device is operated by an internal controller. The controller keeps count and track of the used needles and chambers, operates the actuating devices, light emitting devices and detectors, and collects the raw output from the light detectors. The controller also calculates an outcome from the raw data sufficient to determine if the value is in some cases too high or too low. The outcome can be reported by a stored value that is later downloaded for consideration, in a visual analog or digital display on a scale, in a visual or sound-mediated signal giving an indication that the result falls in one of two or more categories (e.g., a. satisfactory, b. alarm; a. satisfactory, b. borderline out-of-acceptable range, c. alarm), or the like.

In one embodiment, the controller has a device for transmitting outcome data or outcome-derived instructions to another device. Such transmission can be for example by wire-mediated electronic communication, Rf signaling, IR signaling, or the like. The other device can comprise a device for delivering therapeutic substances in response to the measured amount of a monitored analyte. The device can also be integrated with, or adapted for coupling with, a personal digital assistant (PDA), such as one of the Palm series of PDAs available from Palm, Inc. (Santa Clara, Calif.; a subsidiary of 3Com).

The controller incorporates a timing device. In some embodiments, the monitoring events (needle actuation, etc.) are triggered according to a pre-established timetable. In other embodiments, the user or medical personnel can program the timetable or choose between two or more pre-established timetables.

Interactions with the controller can be through any number of devices, such as a small-scaled keypad incorporated into the monitoring device, a more limited set of switches such as are used to program a digital watch, by communication with an external device which can have, for example, a more robust input device.

It will be recognized that the various controller functions described here can be incorporated into, for example, one integrated circuit, or multiple integrated circuits or other electronic devices.

Other Device Features

Output devices are incorporated into the monitoring device. These can comprise a visual display, such as an LCD or LED-mediated display, a sound generating device that can emit either simple tones or synthesized speech, electronic devices for transmitting data, and the like.

The energy source for the device can be, for example, a battery, or a small-scaled fuel cell.

Small-scaled solenoids or like pushing devices are described, for example, in Elan Corporation, WO 99/62576.

Tissues or body parts to which the monitoring device can be affixed/secured include wrists, forearms, upper arms, torso, thighs, calves, ankles, and the like. The device is preferably secured with a strap. The device can also be secured with adhesive, which can also be used to supplement the hold gained with a strap. Suitable adhesives, particularly hypoallergenic adhesives, are available for example from the 3M Corporation. The monitoring device can be affixed to a tissue having a low density of pain-sensing nerves, such as the forearm or thigh.

To retract the needle after use, the distal end of the needle can be affixed to a spring, which includes any of a number of devices known to those of skill in the art that store potential energy derived from a displacement, and tending to provide a force favoring a reversal of the displacement. The actuator can thus, when it applies force to move the needle to the extended position, push against the spring, allowing the spring to provide a force favoring the return of the needle to the retracted position once the force from the actuator is removed.

In another embodiment, the housing cannot be reversibly opened such that the analyte monitoring device is disposable. For example, the needles, pushing apparatus, energy source and analysis sites can be within the housing, where the housing cannot be reversibly opened such that the device is adapted for disposable use. Or, the device has a housing adapted to not be re-openable such that the energy source is not replaceable or rechargeable.

Cassette

In one embodiment, the needles, chambers and the lower portion of the monitoring device through which the needles traverse are mounted in a removable cassette. Thus, the more expensive portions of the monitoring device, such as light detection devices and controllers can be reused, while the portions that contact biological fluid are periodically replaced by substituting cassettes. In one embodiment, a power source is mounted in the cassette to assure periodic replacement. In other embodiments, the power source (e.g., battery, fuel cell) is in a separate accessible compartment and is separately periodically replaced.

Calibration Control

In one aspect, the monitoring device has a slot for receiving a control package having one or more chambers containing a calibration control, such as a fixed concentration of the analyte to be monitored (plus control), or components designed to mirror the material components of a sample less the analyte to be monitored (minus control). The monitoring device either senses the presence of the control package to activate a control algorithm, or its interface allows the user to signal to initiate a control algorithm. In such a control algorithm, at least one chamber and associated needle are engaged with a control fluid from the control package. The control fluid tested can be the plus control, or, using two chambers, the plus control and the minus control. The algorithm (a) operates to adjust calculation parameters in light of the control result, (b) operates to adjust the calculation parameters only if a sufficient deviation from norms is encountered, (c) operates to confirm that the monitoring device is within norms or notes a deviation indicating a need to change or service the monitoring device, (d) makes its determination to adjust or indicate a deviation only after conducting a further control assay, or the like.

Enhancement of ISF Recovery

In one embodiment, a near infra-red or visible light emitting device is incorporated into an ISF-drawing device. The emitted light heats the tissue from which ISF will be drawn, resulting in increased ISF recovery. Without limitation to theory, it is believed that one aspect of the increased ISF recovery is increased ISF flow to the heated tissue.

Preferably, the light emitting device, such as a diode or solid-state laser, emits light in the 1.3 to 1.6 micron wavelength range.

Definitions

The following terms shall have, for the purposes of this application, the respective meanings set forth below.

Diaphorase. The name "diaphorase" has been applied to several enzymes which catalyze the oxidation of either beta-NADH or beta-NADPH in the presence of an electron acceptor such as methylene blue or 2,6-dichlorophenol-indophenol. Diaphorases are typically specific for either beta-NADH or beta-NADPH. The pig heart enzyme of Straub (Straub, *Biochem. J.* 3: 787, 1939) has diaphorase (beta-NADH specific) as well as lipoic and lipoamide dehydrogenase activities. The enzyme is reported to be a single protein, but Massey reports that "diaphorase" is may be a denatured lipoamide dehydrogenase. Pre-incubation of the pig heart preparation with $Cu^{++}$ reduces the lipoamide dehydrogenase activity and proportionately increases the beta-NADH diaphorase activity. Massey and Veeger, *Biochim. Biophys. Acta* 48: 33, 1961. Source examples include *Clostridium kluyveri*, Torula yeast, *Bacillus sterothermophilus* and other sources apparent to those of ordinary skill.

Spring. A spring is any device, including the myriad of such devices known in the art, that mechanically stores kinetic energy as potential energy.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A wearable device constructed for automated detection of the concentration of an analyte present in a sampled body fluid, the device comprising:
    a housing;
    at least one needle adapted to pierce the skin;
    at least one analysis site associated with the at least one needle;
    a processor;
    detection elements wherein the processor accepts data from the detection elements and derives normalized values therefrom; and
    a controller constructed to monitor and control the device in a manner such that repeated detection of the concentration of the analyte present in the sampled body fluid can occur without the necessity of intervention by a wearer of the device.

2. The device of claim 1, wherein the wearer is a human, and device is wearable on one or more of the flowing areas of the body: wrists, forearms, upper arms, torso, thighs, calves, and ankles.

3. The device of claim 1, further comprising a strap for securing the device to the body.

4. The device of claim 1, further comprising an adhesive for securing the device to the body.

5. The device of claim 1, wherein the analyte comprises glucose.

6. The device of claim 5, wherein the body fluid comprises at least one of: interstitial fluid and blood.

7. The device of claim 1, wherein the housing is constructed such that it is not reversibly openable by the wearer, whereby the entire device is disposable.

8. The device of claim 1, further comprising:
    an energy source; and
    detection elements.

9. The device of claim 8, wherein the energy source is removable from the housing.

10. The device of claim 1, further comprising a cassette which is removable from the housing.

11. The device of claim 10, wherein the at least one needle and the at least one analysis site are mounted in the cassette.

12. The device of claim 11, wherein the power source is also mounted in the cassette.

13. The device of claim 1, wherein the at least one needle comprises a microneedle.

14. The device of claim 13, wherein the microneedle has a diameter of 200 µm or less.

15. The device of claim 13, wherein the microneedle has a diameter of 150 µm or less.

16. The device of claim 13, wherein the microneedle has a diameter of 100 µm or less.

17. The device of claim 13, wherein the microneedle has a diameter of 50 µm or less.

18. The device of claim 13, wherein the microneedle has a diameter of 25 µm or less.

19. The device of claim 13, wherein the microneedle is constructed from plastic, glass, silicon wafer, sapphire, quartz, or metal.

20. The device of claim 1, further comprising at least one actuator associated with the at least one needle.

21. The device of claim 20, wherein the actuator comprises at least one of a spring or electrically-driven device.

22. The device of claim 1, wherein the at least one analysis site comprises a support carrying a chemical reagent.

23. The device of claim 22, wherein the support comprises a porous membrane.

24. The device of claim 23, wherein the porous membrane has a pore density such that a beam of light incident therein sees a uniform density of pores.

25. The device of claim 23, wherein the membrane is constructed of nylon, polycarbonate, or polyvinylidene difluoride.

26. The device of claim 22, wherein the analysis site further comprises at least one light source and at least one light detector.

27. The device claim of claim 26, wherein the at least one light source comprises at least one LED.

28. The device of claim 26, wherein at least one light detector comprises at least one charge-coupled device, photodiode, or photodetector.

29. The device of claim 22, further comprising:
    an array of individually addressable light emitting diodes; and
    a charge-coupled device array, photodiode array, or photodetector array.

30. The device of claim 1, further comprising a visual display.

31. The device of claim 1, further comprising a sound generating device.

32. The device of claim 31, wherein the sound generating device can emit tones or synthesized speech.

33. The device of claim 1, further comprising a device for transmitting data or instructions to another device.

34. The device of claim 33, wherein the device for transmitting communicates via wire-mediated electronic communication, Rf signaling, or IR signaling.

35. The device of claim 33, wherein the other device comprises a device for delivering therapeutic substances, or a personal digital assistant.

36. The device of claim 1, further comprising a control package.

37. The device of claim 36, wherein the control package comprises a calibration control having a fixed concentration of the analyte.

38. The device of claim 1, further comprising a device for heating tissue from which the body fluid is to be sampled.

39. The device of claim 1, further comprising at least one near infra-red or visible light source adapted to heat tissue of the wearer.

40. A wearable device constructed for automated detection of the concentration of an analyte present in a sampled body fluid, the device comprising:
   a housing;
   a plurality of microneedles adapted to pierce the skin;
   a plurality of analysis sites associated with the plurality of the microneedles; and
   a controller constructed to monitor and control the device in a manner such that repeated detection of the concentration of the analyte present in the sampled body fluid can occur without the necessity of intervention by a wearer of the device.

41. The device of claim 40, wherein the plurality comprises at least 32 needles and associated analysis sites.

42. The device of claim 40, wherein the plurality comprises at least 160 needles and associated analysis sites.

43. The device of claim 40, wherein each of the plurality of microneedles is extendable to an extent sufficient to pierce the skin of the wearer.

44. A wearable device constructed for automated detection of the concentration of an analyte present in a sampled body fluid, the device comprising:
   a housing;
   at least one needle adapted to pierce the skin;
   at least one analysis site associated with the at least one needle, the at least one analysis site comprises at least one chamber constructed of plastic, glass, silicon or quartz; and
   a controller constructed to monitor and control the device in a manner such that repeated detection of the concentration of the analyte present in the sampled body fluid can occur without the necessity of intervention by a wearer of the device.

45. The device of claim 44, wherein the chamber is windowed.

46. The device of claim 44, wherein the chamber is sized to draw a volume of body fluid of approximately 5,000 nL or less.

47. The device of claim 46, wherein the chamber is sized to draw a volume of body fluid of approximately 300 nL or less.

48. The device of claim 44, further comprising a septum attached to the chamber.

49. The device of claim 48, wherein the chamber is evacuated.

50. The device of claim 49, wherein the needle comprises a first end adapted to puncture the skin of the wearer, and a second end adapted to puncture the septum, thereby allowing the vacuum with the chamber to be applied to the interior of the needle.

51. The device of claim 49, wherein the needle comprises a first end adapted to puncture the skin of the wearer, and a side hole adapted to communicate with the vacuum existing within the chamber.

52. The device of claim 44, further comprising a pump associated with the at least one chamber for evacuating the chamber.

53. A wearable device constructed for automated detection of the concentration of an analyte present in a sampled body fluid, the device comprising:
   a housing;
   at least one needle adapted to pierce the skin;
   at least one analysis site associated with the at least one needle, the at least one analysis site comprises a reagent adapted to react with the analyte to produce a detectable signal, and capable of producing an optically readable signal upon reaction with the analyte; and
   a controller constructed to monitor and control the device in a manner such that repeated detection of the concentration of the analyte present in the sampled body fluid can occur without the necessity of intervention by a wearer of the device.

54. The device of claim 53, wherein the reagent creates a fluorescent signal upon reaction with the analyte.

55. A wearable device constructed for automated detection of the concentration of an analyte present in a sampled body fluid, the device comprising:
   a housing;
   at least one needle adapted to pierce the skin;
   at least one analysis site associated with the at least one needle;
   at least once actuating device;
   at least one light emitting device;
   at least one light detection element;
   a controller constructed to monitor and control the device in a manner such that repeated detection of the concentration of the analyte present in the sampled body fluid can occur without the necessity of intervention by a wearer of the device; and
   wherein the controller keeps track of the number of used needles and analysis sites, operates the at least one actuating device, operates the at least one light emitting device, and collects raw data from the at least one light detection element and performs calculations therewith.

56. A method for periodically and automatically detecting concentration of an analyte present in a sampled body fluid, the method comprising:
   (i) attaching an analyte monitoring device to a wearer, the device comprising at least one needle, at least one analysis site associated with the at least one needle, and a controller;
   (ii) causing the at least one needle to penetrate the skin of the wearer;
   (iii) transporting a sample of body fluid to the at least one analysis site using capillary action;
   (iv) performing an assay on the sample thereby determining the concentration of the analyte in the sample of body fluid.

57. The method of claim 56, wherein steps (ii)–(iv) are governed by the controller such that they are performed without the necessity of intervention by a wearer of the device.

58. The method of claim 56, wherein step (i) comprises attaching the device to the wrist, upper arm, torso, thighs, calves, or ankles of the wearer.

59. The method of claim 56, wherein the analyte comprises glucose and the body fluid comprises interstitial fluid or blood.

60. The method of claim 56, wherein the needle comprises a microneedle.

61. The method of claim 56, wherein step (ii) comprises actuating the needle with at least one of a spring or electrically driven device.

62. The method of claim 56, wherein steps (iii) comprises using a vacuum to facilitate transportation of the sample to the analysis site.

63. The method of claim 56, wherein step (iv) comprise reacting the sample of body fluid with a chemical reagent, producing an optically readable signal, detecting the signal to provide data, and calculating a result therefrom.

64. The method of claim 56, further comprising the step of:
(v) transmitting data obtained from step (iv) to another device.

65. The method of claim 64, wherein step (v) comprises wire-mediated transmission, Rf signaling, or IR signaling.

66. The method of claim 64, wherein the other device comprises a device for the delivery of therapeutic substances or a personal data assistant.

67. A method for automatically detecting concentration of an analyte present in a sampled body fluid, the method comprising:
(i) attaching an analyte monitoring device to a wearer, the device comprising a least one analysis site, and a controller;
(ii) obtaining a sample of body fluid from the wearer;
(iii) transporting the sample of body fluid to the at least one analysis site using capillary action;
(iv) performing an assay on the sample for determining the concentration of the analyte in the sample of body fluid; and
(v) automatically repeating steps (ii)–(iv) without the necessity of intervention by the wearer.

68. The method of claim 67, wherein step (v) is initiated by the controller.

69. The method of claim 67, wherein step (ii) comprises causing at least one of a plurality of microneedles to pierce the skin of the wearer.

70. The method of claim 69, wherein step (ii) comprises actuating the microneedle with at least one of a spring or electrically driven device.

71. The method of claim 67, wherein step (i) comprises attaching the device to the wrist, upper arm, torso, thighs, calves, or ankles of the wearer.

72. The method of claim 67, wherein the analyte comprises glucose and body fluid comprises interstitial fluid or blood.

73. The method of claim step (iii) comprises using a vacuum to facilitate transportation of the sample to the analysis site.

74. The method of claim 67, wherein step (iv) comprises reacting the sample of body fluid with a chemical reagent, producing an optically readable signal, detecting the signal to produce data, and calculating results therefrom.

75. The method of claim 67, further comprising the step of transmitting data obtained from step (iv) to another device.

76. The method of claim 75, wherein the step of transmitting data comprises wire-mediated transmission, Rf signaling, or IR signaling.

77. The method of claim 75, wherein the other device comprises a device for the delivery of therapeutic substances or a personal data assistant.

78. A wearable device constructed for automated periodic detection of the concentration of glucose present in a sampled body fluid, the device comprising:
a housing;
at least one micro-needle adapted to pierce the skin;
at lease one reagent associated with the at least once micro-needle; and
a controller constructed to monitor and control the device in a manner such that repeated periodic detection of the concentration of glucose present in the sampled body fluids occurs at predetermined times without the necessity of intervention by a wearer of the device.

79. The device of claim 78, wherein the wearer is a human.

80. The device of claim 78, wherein the body fluid comprises at least one of blood and interstitial fluid.

81. The device of claim 78, further comprising a housing and a cartridge, the cartridge being separable from the housing.

82. The device of claim 81, wherein the at least one micro-needle and the at least one reagent is disposed in the cartridge.

83. The device of claim 82, wherein the device further comprises a battery, the battery being disposed in the cartridge.

84. The device of claim 83, wherein the device further comprises sensors, the sensors being disposed within the housing.

85. The device of claim 84, wherein the device further comprises electronic components, the electronic components being disposed within the housing.

86. The device of claim 78, wherein the at least one micro-needle is formed from metal.

87. The device of claim 78, wherein the at least one micro-needle comprises an array of micro-needles.

88. The device of claim 78, further comprising at least one of a display, a keypad, and an alarm.

89. The device of claim 78, further comprising an infrared radiation source.

90. A method for automatically detecting concentration of glucose present in a sampled body fluid, the method comprising:
(i) attaching a glucose monitoring device to a wearer, the device comprising at least one micro-needle and at least one reagent associated with the at least one micro-needle, and a controller;
(ii) obtaining a sample of body fluid from the wearer;
(iii) transporting the sample of body fluid to the reagent;
(iv) performing an assay on the sample for determining the concentration of glucose in the sample of body fluid; and
(v) automatically repeating steps (ii)–(iv) without the necessity of intervention by the wearer.

91. The method of claim 90, wherein step (ii) further comprises extending a micro-needle into the skin of the wearer at a predetermined time.

92. The method of claim 91, further comprising the step of withdrawing the micro-needle from the skin of the wearer.

93. The method of claim 90, wherein step (iii) further comprises wicking the sample to the reagent.

94. The method of claim 90, further comprising the step of displaying the concentration of glucose measure in step (iv).

95. The method of claim 90, further comprising generating an alarm when the concentration of glucose measured in step (iv) falls below a predetermined value.

96. The method of claim 90, further comprising transmitting data to another device.

97. The method of claim 96, wherein in data comprises the glucose concentration measured in step (iv).

* * * * *